(12) United States Patent
Adams et al.

(10) Patent No.: US 9,469,880 B2
(45) Date of Patent: Oct. 18, 2016

(54) TRANSGENIC CORN EVENT MON87403 AND METHODS FOR DETECTION THEREOF

(71) Applicant: MONSANTO TECHNOLOGY, LLC, St. Louis, MO (US)

(72) Inventors: Thomas R. Adams, Stonington, CT (US); John A. Korte, Westerly, RI (US); Anagha M. Sant, St. Louis, MO (US); J. Philip Taylor, Saint Peters, MO (US)

(73) Assignee: Monsanto Technology LLC, St. Louis, MO (US)

(*) Notice: Subject to any disclaimer, the term of this patent is extended or adjusted under 35 U.S.C. 154(b) by 59 days.

(21) Appl. No.: 14/507,734

(22) Filed: Oct. 6, 2014

(65) Prior Publication Data
US 2015/0101076 A1 Apr. 9, 2015

Related U.S. Application Data

(60) Provisional application No. 61/888,978, filed on Oct. 9, 2013.

(51) Int. Cl.
*C12Q 1/68* (2006.01)
*C07K 14/415* (2006.01)
*C12N 15/82* (2006.01)

(52) U.S. Cl.
CPC ........... *C12Q 1/6895* (2013.01); *C07K 14/415* (2013.01); *C12N 15/8261* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 5,627,061 | A | 5/1997 | Barry et al. |
| 6,248,876 | B1 | 6/2001 | Barry et al. |
| 7,511,190 | B2 | 3/2009 | Creelman et al. |
| 7,674,955 | B2 | 3/2010 | Chan et al. |
| 8,895,818 | B2 | 11/2014 | Chomet et al. |
| 2005/0283856 | A1 | 12/2005 | Conner et al. |
| 2006/0179511 | A1 | 8/2006 | Chomet et al. |
| 2007/0054278 | A1 | 3/2007 | Cargill |
| 2007/0214517 | A1 | 9/2007 | Alexandrov et al. |
| 2008/0313756 | A1 | 12/2008 | Zhang et al. |
| 2009/0205085 | A1 | 8/2009 | Goldman et al. |
| 2010/0083402 | A1 | 4/2010 | Heard et al. |
| 2011/0252501 | A1 | 10/2011 | Abad et al. |
| 2012/0276074 | A1 | 11/2012 | Scharenberg et al. |
| 2015/0047069 | A1 | 2/2015 | Chomet et al. |

FOREIGN PATENT DOCUMENTS

| | | |
|---|---|---|
| CA | 2456979 | 6/2014 |
| CN | 100999549 | 12/2010 |
| EP | 1797754 | 10/2010 |
| WO | WO 02/16655 | 2/2002 |
| WO | WO 2006/069017 | 6/2006 |
| WO | WO 2007/023190 | 3/2007 |
| WO | WO 2008/015263 | 2/2008 |
| WO | WO 2009/049373 | 4/2009 |
| WO | WO 2011/088065 | 7/2011 |
| WO | PCT/US14/58594 | 10/2014 |

OTHER PUBLICATIONS

Lai et al. (GenBank Accession No. GE573225.1; p. 1; published Nov. 3, 2008).*
Clarke et al., "A colony bank containing synthetic Col El hybrid plasmids representative of the entire *E. coil* genome," *Cell* 9:91-99, 1976.
Dubose et al., "Use of microarray hybrid capture and next-generation sequencing to identify the anatomy of a transgene," *Nucleic Acids Research* 41:e70-e70, 2013.
Salomon et al., "Capture of genomic and T-DNA sequences during double-strand break repair in somatic plant cells," *EMBO Journal* 17:6086-6095, 1998.
Kovalic et al., "The use of next generation sequencing and junction sequence analysis bioinformatics to achieve molecular characterization of crops improved through modern biotechnology," *Plant Genome J* 5:149-163 , 2012.
Lamppa et al., "Structure and developmental regulation of a wheat gene encoding the major chlorophyll a/b-binding polypeptide," *Mol Cell Biol* 5. 1370-1378, 1985.
Odell et al., "Identification of DNA sequences required for activity of the cauliflower mosaic virus 35S promoter," *Nature* 313:810-812, 1985.
Turchi et al., "Arabidopsis HD-Zip II transcription factors control apical embryo development and meristem function," Development 140:2118-2129, 2013.
Ciarbelli et al., "The Arabidopsis homeodomain-leucine zipper II gene family: diversity and redundancy," Plant Mol Biol 68:465-478, 2008.
Harris et al., "Modulation of plant growth by HD-Zip class I and II transcription factors in response to environmental stimuli," New Phytol 190:823-837, 2011.
Ikeda et al., "A novel group of transcriptional repressors in Arabidopsis," Plant Cell Physiol 50(5):970-975, 2009.
Park et al., "ATHB17 is a positive regulator of abscisic acid response during early seedling growth," Mol Cells 35:125-133, 2013.
Bou-Torrent et al., "ATBH4 and HAT3, two class II HD-Zip transcription factors, control leaf development in Arabidopsis," Plant Signal Behavior 7(11):1382-1387, 2012.

(Continued)

*Primary Examiner* — Vinod Kumar
(74) *Attorney, Agent, or Firm* — Dentons US LLP; David Lanzotti, Esq.

(57) ABSTRACT

The present disclosure provides a transgenic corn comprising event MON87403 that exhibits increased grain yield. The disclosure also provides cells, plant parts, seeds, plants, commodity products related to the event, and DNA molecules that are unique to the event and were created by the insertion of transgenic DNA into the genome of a corn plant. The disclosure further provides methods for detecting the presence of said corn event nucleotide sequences in a sample, probes and primers for use in detecting nucleotide sequences that are diagnostic for the presence of said corn event.

22 Claims, 4 Drawing Sheets

(56) References Cited

OTHER PUBLICATIONS

Zhao et al., "Systematic analysis of sequences and expression patterns of grought-responsive members of the HD-Zip gene family in maize," PLoS One 6(12):e28488, 2011.
U.S. Appl. No. 14/511,095, filed Oct. 9, 2014, Ahrens et al.
U.S. Appl. No. 61/888,980, filed Oct. 9, 2013, Griffith et al.
Ariel et al., "The true story of the HD-Zip family," *Trends in Plant Science* 12(9):419-426, 2007.
Barker et al., "Nucleotide sequence of the T-DNA region from the *Agrobacterium tumefaciens* octopine Ti plasmid pTi15955," *Plant Molecular Biology* 2:335-350, 1983.
Bevan et al., "Structure and transcription of the nopaline synthase gene region of T-DNA," *Nucleic Acids Research* 11(2):369-385,1983.
Depicker et al, "Nopaline synthase: transcript mapping and DNA sequence," *Journal of Molecular and Applied Genetics* 1(6):561-573, 1982.
Fling et al., "Nucleotide sequence of the transposon Tn7 gene encoding an aminoglycoside-modifying enzyme, 3"(9)-O-nucleotidyltransferase," *Nucleic Acids Research* 13(19):7095-7106, 1985.
Fraley et al., "Expression of bacterial genes in plant cells," :*PNAS USA* 80:4803-4807, 1983.
Giza and Huang, "A self-inducing runaway-replication plasmid expression system utilizing the Rop protein," *Gene* 78:73-84, 1989.
Hermann, "The shikimate pathway as an entry to aromatic secondary metabolism," *Plant Physiol* 107:7-12, 1995.
Hymus et al., "Application of HB17, an Arabidopsis class II homeodomain-leucine zipper transcription factor, to regulate chloroplast number and photosynthetic capacity," *Journal of Experimental Botany* 64(14):4479-4490, 2013.
International Search Report and Written Opinion regarding International Application No. PCT/US2014/058585, dated Feb. 4, 2015.
Kay et al., "Duplication of CaMV 35S promoter sequences creates a strong enhancer for plant genes," *Science* 236(4806):1299-1302, 1987.
Klee et al., "Cloning of an *Arabidopsis thaliana* gene encoding 5-enolpyruvylshikimate-3-phosphate synthase: sequence analysis and manipulation to obtain glyphosate-tolerant plants," *Mol Gen Genet* 210(3):437-442, 1987.
McElroy et al., "Isolation of an efficient actin promoter for use in rice transformation," *Plant Cell* 2:163-171, 1990.
McElroy et al., "Construction of expression vectors based on the rice actin 1 (Act1) 5' region for use in monocot transformation," *Mol Gen Genet* 231:150-160, 1991.
McElwain and Spiker, "A wheat cDNA clone which is homologous to the 17 kd heat-chock protein gene family of soybean," *Nucleic Acids Res* 17(4):1764-1764, 1989.
Padgette et al., "New weed control opportunities: development of soybeans with Roundup Ready TM gene," In: Herbicide Resistant Crops, Padgette et al. (Eds.), CRC Press Inc., pp. 53-84, London, UK, 1996.
Rice et al., "Expression of a Truncated ATHB17 Protein in Maize Increases Ear Weight at Silking," *PLOS One* 9(4):e94238, 2014.
Stalker et al., "Nucleotide Sequence of the Region of the Origin of Replication of the Broad Host Range Plasmid RK2," *Mol. Gen. Genet.* 181:8-12, 1981.
Vieira and Messing, "Production of single-stranded plasmid DNA," *Methods in Enzymology* 153:3-11, 1987.
Zambryski et al., "Tumor induction by *Agrobacterium tumefaciens*: Analysis of the boundaries of T-DNA," *Journal of Molecular and Applied Genetics* 1:361-370, 1982.
GenBank Accession No. NM_126204, dated Jun. 5, 2013.
GenBank Accession No. AJ431181, dated Apr. 22, 2008.
GenBank Accession No. AC005560, dated Mar. 11, 2002.
GenBank Accession No. NP_178252, dated Jun. 5, 2013.
GenBank Accession No. AAC67320, dated Mar. 11, 2002.
Gryson et al., "Detection of DNA During the Refining of Soybean Oil," *JAOCS*; vol. 79, No. 2; 2002.
U.S. Appl. No. 15/028,381, filed Apr. 8, 2016, Griffith et al.

\* cited by examiner

SEQUENCE LISTING

```
<160> NUMBER OF SEQ ID NOS: 29

<210> SEQ ID NO 1
<211> LENGTH: 20
<212> TYPE: DNA
<213> ORGANISM: Zea mays

<400> SEQUENCE: 1
tgatgttttt actgaaggcg                                           20

<210> SEQ ID NO 2
<211> LENGTH: 20
<212> TYPE: DNA
<213> ORGANISM: Zea mays

<400> SEQUENCE: 2
tactcattgc gatccacatt                                           20

<210> SEQ ID NO 3
<211> LENGTH: 60
<212> TYPE: DNA
```

<213> ORGANISM: Zea mays

<400> SEQUENCE: 3

```
tacttaatat gggcacacag tgatgttttt actgaaggcg ggaaacgaca atctggcgcg    60
```

<210> SEQ ID NO 4
<211> LENGTH: 60
<212> TYPE: DNA
<213> ORGANISM: Zea mays

<400> SEQUENCE: 4

```
tttctccata ttgaccatca tactcattgc gatccacatt tccctacatg gtggaggata    60
```

<210> SEQ ID NO 5
<211> LENGTH: 100
<212> TYPE: DNA
<213> ORGANISM: Zea mays

<400> SEQUENCE: 5

```
tatgaaccca taaaactgaa tacttaatat gggcacacag tgatgttttt actgaaggcg    60
ggaaacgaca atctggcgcg cctgcctgca ggcatcgttg                         100
```

<210> SEQ ID NO 6
<211> LENGTH: 100
<212> TYPE: DNA
<213> ORGANISM: Zea mays

<400> SEQUENCE: 6

```
attggtaatt actctttctt tttctccata ttgaccatca tactcattgc gatccacatt    60
tccctacatg gtggaggata cagagcactc attccggagt                         100
```

<210> SEQ ID NO 7
<211> LENGTH: 3000
<212> TYPE: DNA
<213> ORGANISM: Zea mays

<400> SEQUENCE: 7

```
ctactatttt ggaacagagg gaatagtagg tagtaatgtt tcacaataaa tcacagtgct    60
aaaatgagat atgaccttag atcccatagc tcattgcata aaagtacttg atcagttggt   120
cactgtcttt cagaaaaacc gcagtttaat taaacttaat ggctgctgga tcagatgcta   180
gatagcacta tatcttaatt cgttttgcat gaacacctta taatacagaa ccttttcttt   240
tcttccagca actagactct gcatcccttg tggaaatgtg aaccttggtt cgtacatgac   300
aaataataca acatatcatg ctacctatgc aacactgact tgatttcaat ccttggttta   360
cttgccacat catacttatg gtatatttgg gtgaaaagta gatgtttcaa gcagtttgta   420
aatcctaaat acatcatggt ttactctggt gctacaacta ctgttttaag gagaaactat   480
tagctttggg atcatctaga atattagcat agcatcaact tcaggcacaa ctacaagagc   540
agcacttgaa ggggtaaaat tcagtgctac ctacgtaaat cataaaaaaa attatttgtt   600
tgaattcaag tgttttgggg gttcaacaat gattctatgt agctataaat ttttttgttg   660
atttcatgtc atattgatta ttggtttgat ttcacctgtt ttcttattgt cagccagaac   720
cagcttacta tttcggatgt tgcaaggaag gcattccttc acagtgtatg tgatagttct   780
ctttatacat gtaagacagt gtacaagggc aaaactttgt atgaaattac tctgtactgt   840
ttacaatgat tacagggcat acttgtagtg tttgaggagc aagagacaaa actctacatt   900
ttagatatat aaagcaatag ttctttaact caaaccaaaa tctggattag tcttgagcac   960
```

```
tttctaataa tcatataatg ctcatgtacc tcaataactg cttcagttaa tcacatcttt    1020
tagtttagca ctatgctatg atagtttaca aagtgcattg ttagcttatt ttccccatag    1080 gttcttttaat catatctatt gtgctagatt ttactctgtc ccattaggag acaaacaagt   1140
tcgttcaata gcatatgaca cttgtatgct ggtaaaatga ttgaatattt tgtttgacac    1200
ctattgtttg aaggatgtaa gcaatctcat gtacctgttg ttgctcgcaa ggttcatccc    1260
tcacaagtac aagatcaaag actcgaaagc ttaggtatga acccataaaa ctgaatactt    1320
aatatgggca cacagtgatg tttttactga aggcgggaaa cgacaatctg gcgcgcctgc    1380
ctgcaggcat cgttgaagat gcctctgccg acagtggtcc caagatggac ccccacccca   1440
cgaggagcat cgtggaaaaa gaagacgttc aaccacgtc ttcaaagcaa gtggattgat     1500
gtgatatctc cactgacgta agggatgacg cacaatccca ctatccttcg aggcctcatc   1560
gttgaagatg cctctgccga cagtggtccc aaagatggac ccccacccac gaggagcatc   1620
gtggaaaaag aagacgttcc aaccacgtct tcaaagcaag tggattgatg tgatatctcc    1680
actgacgtaa gggatgacgc acaatcccac tatccttcga agcttactcg aggtcattca   1740
tatgcttgag aagagagtcg ggatagtcca aaataaaaca aaggtaagat tacctggtca   1800
aaagtgaaaa catcagttaa aaggtggtat aaagtaaaat atcggtaata aaaggtggcc    1860
caaagtgaaa tttactcttt tctactatta taaaaattga ggatgttttt gtcggtactt    1920
tgatacgtca tttttgtatg aattggtttt taagtttatt cgcttttgga aatgcatatc   1980
tgtatttgag tcgggtttta agttcgtttg cttttgtaaa tacagaggga tttgtataag   2040
aaatatcttt agaaaaaccc atatgctaat ttgacataat ttttgagaaa aatatatatt   2100
caggcgaatt ctcacaatga acaataataa gattaaaata gctttccccc gttgcagcgc   2160
atgggtattt tttctagtaa aaataaaaga taaacttaga ctcaaaacat ttacaaaaac    2220 aaccctaaa gttcctaaag cccaaagtgc tatccacgat ccatagcaag cccagcccaa     2280
cccaacccaa cccaacccac cccagtccag ccaactggac aatagtctcc acccccccc    2340 actatcaccg tgagttgtcc gcacgcaccg cacgtctcgc agccaaaaaa aaaagaaag    2400 aaaaaaaaga aaaagaaaaa acagcaggtg ggtccgggtc gtgggggccg gaaacgcgag   2460
gaggatcgcg agccagcgac gaggccggcc ctccctccgc ttccaaagaa acgccccca    2520 tcgccactat atacataccc cccctctcc tcccatcccc caacccttc tagaaccatc      2580 ttccacacac tcaagccaca ctattggaga acacacaggg acaacacacc ataagatcca   2640
agggaggcct ccgccgccgc cggtaaccac cccgcccctc tcctctttct ttctccgttt    2700 tttttttccgt ctcggtctcg atctttggcc ttggtagttt gggtgggcga gaggcggctt   2760
cgtgcgcgcc cagatcggtg cgcgggaggg gcgggatctc gcggctgggg ctctcgccgg   2820
cgtggatccg gcccggatct cgcggggaat ggggctctcg gatgtagatc tgcgatccgc   2880
cgttgttggg ggagatgatg ggggggttaa aatttccgcc gtgctaaaca agatcaggaa   2940 gagggggaaaa gggcactatg gtttatattt ttatatattt ctgctgcttc gtcaggctta    3000
```

<210> SEQ ID NO 8
<211> LENGTH: 2624
<212> TYPE: DNA
<213> ORGANISM: Zea mays

<400> SEQUENCE: 8

```
taggtagaag cggaccggta ccatgataaa actactattt acgtacatat gcacatacac      60
```

-continued

```
atataaacta tatgctctat atcatatgga ttacgcatgc gtgtgtatgt ataaatataa      120
aggcatcgtc acgcttcaag tttgtctctt ttatattaaa ctgagagttt cctctcaaa      180 ctttaccttt tcttcttcga tcctagctct taagaaccct aataattcat tgatcaaaat     240
aatggcgatt ttgccggaaa actcttcaaa cttggatctt actatctccg ttccaggctt     300
ctcttcatcc cctctctccg atgaaggaag tggcggagga agagaccagc taaggctaga     360
catgaatcgg ttaccgtcgt ctgaagacgg agacgatgaa gaattcagtc acgatgatgg     420
ctctgctcct ccgcgaaaga aactccgtct aaccagagaa cagtcacgtc ttcttgaaga     480
tagtttcaga cagaatcata cccttaatcc caaacaaaag gaagtacttg ccaagcattt     540
gatgctacgg ccaagacaaa ttgaagtttg gtttcaaaac cgtagagcaa ggagcaaatt     600
gaagcaaacc gagatggaat gcgagtatct caaaaggtgg tttggttcat taacggaaga     660
aaaccacagg ctccatagag aagtagaaga gcttagagcc ataaaggttg gcccaacaac     720
ggtgaactct gcctcgagcc ttactatgtg tcctcgctgc gagcgagtta cccctgccgc     780
gagcccttcg agggcggtgg tgccggttcc ggctaagaaa acgtttccgc cgcaagagcg     840
tgatcgttga gtcggggccc gggctgcatg cgtttggacg tatgctcatt caggttggag     900
ccaatttggt tgatgtgtgt gcgagttctt gcgagtctga tgagacatct ctgtattgtg     960 tttcttttccc cagtgttttc tgtacttgtg taatcggcta atcgccaaca gattcggcga    1020
tgaataaatg agaaataaat tgttctgatt ttgagtgcaa aaaaaaagga attaagctta    1080
ctcgagatcc actagtgatt aagcggccgc atcgatcgtg aagtttctca tctaagcccc    1140
catttggacg tgaatgtaga cacgtcgaaa taaagatttc cgaattagaa taatttgttt    1200
attgctttcg cctataaata cgacggatcg taatttgtcg ttttatcaaa atgtactttc    1260
attttataat aacgctgcgg acatctacat ttttgaattg aaaaaaaatt ggtaattact    1320
cttttctttt ctccatattg accatcatac tcattgcgat ccacatttcc ctacatggtg    1380
gaggatacag agcactcatt ccggagtata atcttgtctt gtgttgccac ctatttatca    1440
cttgagcata tacaatgaat gtttcttaag atgtcaatat ttgcttataa tatagtgact    1500
tcccagtata tgtttcagtt ttgtttcttg cttagtgact agaacaaaaa acaagtgtt    1560 ctattggttt aattaatcta aactgcattg ctcaagcaat aattgagttt attccctata    1620
acttgcaaag tgtggccatg ttatgccctg tggctgtgcg tggccatctg acctccacat    1680
ctatgtttcc cactgctagg ttgctttgag tcgtggtgga tctcccggtg tgacgacatg    1740
gggctgggtc tgggagctct tctcaaatcc gcgggctctc ggtctgctct tctcaattta    1800
gtgttatctt tttcttttag aacaatgcca agaaacatg acagactgct tgcttgttt    1860 ttgacatgat gcaaaagcaa tggagtcttt acttttaaac ctttgtattt ttgttttgat    1920
tcaattctga tactgctgaa atgtacgaat atctattatt ttgatgcaat agtggtgttt    1980
tgcgatgttt aacagcttgt gtaatccaat tattaaccct gctttgtata gaagagtttc    2040
ttcagaatat atcaattcat gtattctcat tatggatatt atgtggatat tttctatcta    2100
tgaatggccc ctgcactttg aatcgcttat gtcattgtta gcaatcacat aatatttttc    2160
ttttctctta gatttaattt gtataatcat ataatcattc atatattgtt acaacaggat    2220
ttggttcagc ttctcacttt gttttaattc tgatactgct ggttctcttc ttgccaggtg    2280
cgtgcggcca cccggccgtg gaccaagcgc cgccgctgct cttcttgcca ggtgcgtgcg    2340
tctcttcagc tggccaaaat caatcatccc aatgcttgtt tctgaagggc agcatgtagc    2400
tcgaggtgct ggtcaaacgg aggaatcatt ctggtttggt ttctctttg ttttgtaca    2460
```

| | |
|---|---|
| tagatgacga cgacgtgtct cccgatgcct ccccgtcact ggcacacctt ggcatcgatc | 2520 |
| ctcgaatctc tacccccaca cccacatctc cccgctgccg aaccagcccc gatttgccac | 2580 |
| catggacgtc gatgacgtat cacccaatgt ctccctgtct ctgg | 2624 |

<210> SEQ ID NO 9
<211> LENGTH: 3132
<212> TYPE: DNA
<213> ORGANISM: Zea mays

<400> SEQUENCE: 9

| | |
|---|---|
| actgaaggcg ggaaacgaca atctggcgcg cctgcctgca ggcatcgttg aagatgcctc | 60 |
| tgccgacagt ggtcccaaag atggacccca cccacgagg agcatcgtgg aaaaagaaga | 120 |
| cgttccaacc acgtcttcaa agcaagtgga ttgatgtgat atctccactg acgtaaggga | 180 |
| tgacgcacaa tcccactatc cttcgaggcc tcatcgttga agatgcctct gccgacagtg | 240 |
| gtcccaaaga tggaccccca cccacgagga gcatcgtgga aaaagaagac gttccaacca | 300 |
| cgtcttcaaa gcaagtggat tgatgtgata tctccactga cgtaagggat gacgcacaat | 360 |
| cccactatcc ttcgaagctt actcgaggtc attcatatgc ttgagaagag agtcgggata | 420 |
| gtccaaaata aacaaaggt aagattacct ggtcaaaagt gaaaacatca gttaaaaggt | 480 |
| ggtataaagt aaaatatcgg taataaaagg tgggcccaaag tgaaatttac tcttttctac | 540 |
| tattataaaa attgaggatg ttttgtcgg tactttgata cgtcattttt gtatgaattg | 600 |
| gttttttaagt ttattcgctt ttggaaatgc atatctgtat ttgagtcggg ttttaagttc | 660 |
| gtttgctttt gtaaatacag agggatttgt ataagaaata tctttagaaa aacccatatg | 720 |
| ctaatttgac ataattttg agaaaaatat atattcaggc gaattctcac aatgaacaat | 780 |
| aataagatta aaatagcttt cccccgttgc agcgcatggg tattttttct agtaaaaata | 840 |
| aaagataaac ttagactcaa acatttaca aaaacaaccc ctaaagttcc taaagcccaa | 900 |
| agtgctatcc acgatccata gcaagcccag cccaacccaa cccaacccaa ccacccag | 960 |
| tccagccaac tggacaatag tctccacacc ccccactat caccgtgagt tgtccgcacg | 1020 |
| caccgcacgt ctcgcagcca aaaaaaaaaa gaaagaaaaa aagaaaaag aaaaaacagc | 1080 |
| aggtgggtcc gggtcgtggg ggccggaaac gcgaggagga tcgcgagcca gcgacgaggc | 1140 |
| cggccctccc tccgcttcca aagaaacgcc cccatcgcc actatataca tacccccccc | 1200 |
| tctcctccca tcccccaac ccttctagaa ccatcttcca cacactcaag ccacactatt | 1260 |
| ggagaacaca cagggacaac acaccataag atccaaggga ggcctccgcc gccgccggta | 1320 |
| accaccccgc ccctctcctc tttctttctc cgtttttttt tccgtctcgg tctcgatctt | 1380 |
| tggccttggt agtttgggtg ggcgagaggc ggcttcgtgc gcgcccagat cggtgcgcgg | 1440 |
| gaggggcggg atctcgcggc tgggctctc gccggcgtgg atccggcccg gatctcgcgg | 1500 |
| ggaatgggc tctcggatgt agatctgcga tccgccgttg ttgggggaga tgatggggg | 1560 |
| tttaaaattt ccgccgtgct aaacaagatc aggaagaggg gaaaagggca ctatggttta | 1620 |
| tattttata tatttctgct gcttcgtcag gcttagatgt gctagatctt tcttttcttct | 1680 |
| ttttgtgggt agaatttgaa tccctcagca ttgttcatcg gtagttttc ttttcatgat | 1740 |
| ttgtgacaaa tgcagcctcg tgcggagctt ttttgtaggt agaagcggac cggtaccatg | 1800 |
| ataaaactac tatttacgta catatgcaca tacacatata aactatatgc tctatatcat | 1860 |
| atggattacg catgcgtgtg tatgtataaa tataaaggca tcgtcacgct tcaagtttgt | 1920 |

```
ctcttttata ttaaactgag agttttcctc tcaaacttta ccttttcttc ttcgatccta    1980
gctcttaaga accctaataa ttcattgatc aaaataatgg cgattttgcc ggaaaactct    2040
tcaaacttgg atcttactat ctccgttcca ggcttctctt catccctct ctccgatgaa     2100
ggaagtggcg gaggaagaga ccagctaagg ctagacatga atcggttacc gtcgtctgaa    2160
gacggagacg atgaagaatt cagtcacgat gatggctctg ctcctccgcg aaagaaactc    2220
cgtctaacca gagaacagtc acgtcttctt gaagatagtt tcagacagaa tcataccctt    2280
aatcccaaac aaaaggaagt acttgccaag catttgatgc tacggccaag acaaattgaa    2340
gtttggtttc aaaaccgtag agcaaggagc aaattgaagc aaaccgagat ggaatgcgag    2400
tatctcaaaa ggtggtttgg ttcattaacg gaagaaaacc acaggctcca tagagaagta    2460
gaagagctta gagccataaa ggttggccca acaacggtga actctgcctc gagccttact    2520
atgtgtcctc gctgcgagcg agttacccct gccgcgagcc cttcgagggc ggtggtgccg    2580
gttccggcta agaaaacgtt tccgccgcaa gagcgtgatc gttgagtcgg ggcccgggct    2640
gcatgcgttt ggacgtatgc tcattcaggt tggagccaat ttggttgatg tgtgtgcgag    2700
ttcttgcgag tctgatgaga catctctgta ttgtgtttct ttccccagtg ttttctgtac    2760
ttgtgtaatc ggctaatcgc caacagattc ggcgatgaat aaatgagaaa taaattgttc    2820
tgattttgag tgcaaaaaaa aaggaattaa gcttactcga gatccactag tgattaagcg    2880
gccgcatcga tcgtgaagtt tctcatctaa gcccccattt ggacgtgaat gtagacacgt    2940
cgaaataaag atttccgaat tagaataatt tgtttattgc tttcgcctat aaatacgacg    3000
gatcgtaatt tgtcgtttta tcaaaatgta ctttcatttt ataataacgc tgcggacatc    3060
tacatttttg aattgaaaaa aaattggtaa ttactctttc tttttctcca tattgaccat    3120
catactcatt gc                                                         3132

<210> SEQ ID NO 10
<211> LENGTH: 5744
<212> TYPE: DNA
<213> ORGANISM: Zea mays

<400> SEQUENCE: 10
ctactatttt ggaacagagg gaatagtagg tagtaatgtt tcacaataaa tcacagtgct     60
aaaatgagat atgaccttag atcccatagc tcattgcata aaagtacttg atcagttggt    120
cactgtcttt cagaaaaacc gcagtttaat taaacttaat ggctgctgga tcagatgcta    180
gatagcacta tatcttaatt cgttttgcat gaacaccta taatacagaa ccttttcttt     240
tcttccagca actagactct gcatcccttg tggaaatgtg aaccttggtt cgtacatgac    300
aaataataca acatatcatg ctacctatgc aacactgact tgatttcaat ccttggttta    360
cttgccacat catacttatg gtatatttgg gtgaaaagta gatgtttcaa gcagtttgta    420
aatcctaaat acatcatggt ttactctggt gctacaacta ctgttttaag gagaaactat    480
tagctttggg atcatctaga atattagcat agcatcaact tcaggcacaa ctacaagagc    540
agcacttgaa ggggtaaaat tcagtgctac ctacgtaaat cataaaaaaa attatttgtt    600
tgaattcaag tgtttggggg gttcaacaat gattctatgt agctataaat ttttttgttg    660
atttcatgtc atattgatta ttggtttgat ttcacctgtt ttcttattgt cagccagaac    720
cagcttacta tttcggatgt tgcaaggaag gcattcctc acagtgtatg tgatagttct    780
ctttatacat gtaagacagt gtacaagggc aaaactttgt atgaaattac tctgtactgt    840
ttacaatgat tacagggcat acttgtagtg tttgaggagc aagagacaaa actctacatt    900
```

```
ttagatatat aaagcaatag ttctttaact caaaccaaaa tctggattag tcttgagcac    960
tttctaataa tcatataatg ctcatgtacc tcaataactg cttcagttaa tcacatcttt   1020
tagtttagca ctatgctatg atagtttaca aagtgcattg ttagcttatt ttccccatag   1080 gttcttaat catatctatt gtgctagatt ttactctgtc ccattaggag acaaacaagt    1140
tcgttcaata gcatatgaca cttgtatgct ggtaaaatga ttgaatattt tgtttgacac   1200
ctattgtttg aaggatgtaa gcaatctcat gtacctgttg ttgctcgcaa ggttcatccc   1260
tcacaagtac aagatcaaag actcgaaagc ttaggtatga acccataaaa ctgaatactt   1320
aatatgggca cacagtgatg tttttactga aggcgggaaa cgacaatctg gcgcgcctgc   1380
ctgcaggcat cgttgaagat gcctctgccg acagtggtcc caaagatgga cccccaccca   1440
cgaggagcat cgtggaaaaa gaagacgttc caaccacgtc ttcaaagcaa gtggattgat   1500
gtgatatctc cactgacgta agggatgacg cacaatccca ctatccttcg aggcctcatc   1560
gttgaagatg cctctgccga cagtggtccc aaagatggac ccccacccac gaggagcatc   1620
gtggaaaaag aagacgttcc aaccacgtct tcaaagcaag tggattgatg tgatatctcc   1680
actgacgtaa gggatgacgc acaatcccac tatccttcga agcttactcg aggtcattca   1740
tatgcttgag aagagagtcg ggatagtcca aaataaaaca aaggtaagat tacctggtca   1800
aaagtgaaaa catcagttaa aaggtggtat aaagtaaaat atcggtaata aaaggtggcc   1860
caaagtgaaa tttactcttt tctactatta taaaaattga ggatgttttt gtcggtactt   1920
tgatacgtca ttttgtatg aattggtttt taagtttatt cgcttttgga aatgcatatc    1980
tgtatttgag tcgggtttta agttcgtttg cttttgtaaa tacagaggga tttgtataag   2040
aaatatcttt agaaaaaccc atatgctaat ttgacataat ttttgagaaa aatatatatt   2100
caggcgaatt ctcacaatga acaataataa gattaaaata gctttccccc gttgcagcgc   2160 atgggtatt tttctagtaa aaataaaaga taaacttaga ctcaaaacat ttacaaaaac    2220
aacccctaaa gttcctaaag cccaaagtgc tatccacgat ccatagcaag cccagcccaa   2280
cccaacccaa cccaacccac cccagtccag ccaactggac aatagtctcc acacccccc    2340 actatcaccg tgagttgtcc gcacgcaccg cacgtctcgc agccaaaaaa aaaagaaag    2400 aaaaaaaaga aaaagaaaaa acagcaggtg ggtccgggtc gtggggccg gaaacgcgag    2460 gaggatcgcg agccagcgac gaggccggcc ctccctccgc ttccaaagaa cgccccca    2520 tcgccactat atacataccc ccccctctcc tcccatcccc ccaacccttc tagaaccatc   2580
ttccacacac tcaagccaca ctattggaga acacacaggg acaacacacc ataagatcca   2640
agggaggcct ccgccgccgc cggtaaccac cccgcccctc tcctctttct ttctccgttt   2700 tttttttccgt ctcggtctcg atctttggcc ttggtagttt gggtgggcga gaggcggctt   2760
cgtgcgcgcc cagatcggtg cgcgggaggg gcgggatctc gcggctgggg ctctcgccgg   2820
cgtggatccg gcccggatct cgcgggaat ggggctctcg gatgtagatc tgcgatccgc    2880
cgttgttggg ggagatgatg gggggtttaa aatttccgcc gtgctaaaca agatcaggaa   2940 gagggggaaaa gggcactatg gtttatattt ttatatattt ctgctgcttc gtcaggctta   3000
gatgtgctag atctttcttt cttcttttg tgggtagaat ttgaatccct cagcattgtt    3060
catcggtagt ttttctttc atgatttgtg acaaatgcag cctcgtgcgg agctttttg    3120 taggtagaag cggaccggta ccatgataaa actactattt acgtacatat gcacatacac   3180
atataaacta tatgctctat atcatatgga ttacgcatgc gtgtgtatgt ataaatataa   3240
```

```
aggcatcgtc acgcttcaag tttgtctctt ttatattaaa ctgagagttt tcctctcaaa   3300
ctttaccttt tcttcttcga tcctagctct taagaaccct aataattcat tgatcaaaat   3360
aatggcgatt ttgccggaaa actcttcaaa cttggatctt actatctccg ttccaggctt   3420
ctcttcatcc cctctctccg atgaaggaag tggcggagga agagaccagc taaggctaga   3480
catgaatcgg ttaccgtcgt ctgaagacgg agacgatgaa gaattcagtc acgatgatgg   3540
ctctgctcct ccgcgaaaga aactccgtct aaccagagaa cagtcacgtc ttcttgaaga   3600
tagtttcaga cagaatcata cccttaatcc caaacaaaag gaagtacttg ccaagcattt   3660
gatgctacgg ccaagacaaa ttgaagtttg gtttcaaaac cgtagagcaa ggagcaaatt   3720
gaagcaaacc gagatggaat gcgagtatct caaaaggtgg tttggttcat taacggaaga   3780
aaaccacagg ctccatagag aagtagaaga gcttagagcc ataaaggttg gcccaacaac   3840
ggtgaactct gcctcgagcc ttactatgtg tcctcgctgc gagcgagtta cccctgccgc   3900
gagcccttcg agggcggtgg tgccggttcc ggctaagaaa acgtttccgc cgcaagagcg   3960
tgatcgttga gtcgggcccg ggctgcatg cgtttggacg tatgctcatt caggttggag   4020
ccaatttggt tgatgtgtgt gcgagttctt gcgagtctga tgagacatct ctgtattgtg   4080
tttctttccc cagtgttttc tgtacttgtg taatcggcta atcgccaaca gattcggcga   4140
tgaataaatg agaaataaat tgttctgatt ttgagtgcaa aaaaaaagga attaagctta   4200
ctcgagatcc actagtgatt aagcggccgc atcgatcgtg aagtttctca tctaagcccc   4260
catttggacg tgaatgtaga cacgtcgaaa taaagatttc cgaattagaa taatttgttt   4320
attgctttcg cctataaata cgacggatcg taatttgtcg ttttatcaaa atgtactttc   4380
attttataat aacgctgcgg acatctacat ttttgaattg aaaaaaaatt ggtaattact   4440
cttctttttt ctccatattg accatcatac tcattgcgat ccacatttcc ctacatggtg   4500
gaggatacag agcactcatt ccggagtata atcttgtctt gtgttgccac ctatttatca   4560
cttgagcata tacaatgaat gtttcttaag atgtcaatat ttgcttataa tatagtgact   4620
tcccagtata tgtttcagtt ttgtttcttg cttagtgact agaacaaaaa aacaagtgtt   4680
ctattggttt aattaatcta aactgcattg ctcaagcaat aattgagttt attccctata   4740
acttgcaaag tgtggccatg ttatgccctg tggctgtgcg tggccatctg acctccacat   4800
ctatgtttcc cactgctagg ttgctttgag tcgtggtgga tctcccggtg tgacgacatg   4860
gggctgggtc tgggagctct tctcaaatcc gcgggctctc ggtctgctct tctcaattta   4920
gtgttatctt tttctttag aacaatgcca agaaacatg acagactgct ttgcttgttt   4980
ttgacatgat gcaaaagcaa tggagtcttt acttttaaac ctttgtattt ttgttttgat   5040
tcaattctga tactgctgaa atgtacgaat atctattatt ttgatgcaat agtggtgttt   5100
tgcgatgttt aacagcttgt gtaatccaat tattaaccct gctttgtata aagagtttc   5160 ttcagaatat atcaattcat gtattctcat tatggatatt atgtggatat tttctatcta   5220
tgaatggccc ctgcactttg aatcgcttat gtcattgtta gcaatcacat aatattttc   5280 ttttctctta gatttaattt gtataatcat ataatcattc atatattgtt acaacaggat   5340
ttggttcagc ttctcacttt gttttaattc tgatactgct ggttctcttc ttgccaggtg   5400
cgtgcggcca cccggccgtg gaccaagcgc cgccgctgct cttcttgcca ggtgcgtgcg   5460
tctcttcagc tggccaaaat caatcatccc aatgcttgtt tctgaagggc agcatgtagc   5520
tcgaggtgct ggtcaaacgg aggaatcatt ctggtttggt ttctcttttg tttttgtaca   5580
tagatgacga cgacgtgtct cccgatgcct ccccgtcact ggcacacctt ggcatcgatc   5640
```

-continued

```
ctcgaatctc taccccaca cccacatctc cccgctgccg aacccagcccc gatttgccac    5700 catggacgtc gatgacgtat cacccaatgt ctccctgtct ctgg                    5744
```

<210> SEQ ID NO 11
<211> LENGTH: 22
<212> TYPE: DNA
<213> ORGANISM: Artificial sequence
<220> FEATURE:
<223> OTHER INFORMATION: Primer

<400> SEQUENCE: 11

```
tgctctgtat cctccaccat gt                                            22
```

<210> SEQ ID NO 12
<211> LENGTH: 27
<212> TYPE: DNA
<213> ORGANISM: Artificial sequence
<220> FEATURE:
<223> OTHER INFORMATION: Primer

<400> SEQUENCE: 12

```
tttctccata ttgaccatca tactcat                                       27
```

<210> SEQ ID NO 13
<211> LENGTH: 15
<212> TYPE: DNA
<213> ORGANISM: Artificial sequence
<220> FEATURE:
<223> OTHER INFORMATION: Primer

<400> SEQUENCE: 13

```
ctgatccaca tttcc                                                    15
```

<210> SEQ ID NO 14
<211> LENGTH: 27
<212> TYPE: DNA
<213> ORGANISM: Artificial sequence
<220> FEATURE:
<223> OTHER INFORMATION: Primer

<400> SEQUENCE: 14

```
gcatgtcttt aaaaatcctt ggtttac                                       27
```

<210> SEQ ID NO 15
<211> LENGTH: 26
<212> TYPE: DNA
<213> ORGANISM: Artificial sequence
<220> FEATURE:
<223> OTHER INFORMATION: Primer

<400> SEQUENCE: 15

```
tgatgttttt actggattgc attacc                                        26
```

<210> SEQ ID NO 16
<211> LENGTH: 23
<212> TYPE: DNA
<213> ORGANISM: Artificial sequence
<220> FEATURE:
<223> OTHER INFORMATION: Primer

<400> SEQUENCE: 16

```
caccctaaga gtactattga aga                                           23
```

<210> SEQ ID NO 17

```
<211> LENGTH: 27
<212> TYPE: DNA
<213> ORGANISM: Artificial sequence
<220> FEATURE:
<223> OTHER INFORMATION: Primer

<400> SEQUENCE: 17
ttgttgctcg caaggttcat ccctcac                                        27

<210> SEQ ID NO 18
<211> LENGTH: 30
<212> TYPE: DNA
<213> ORGANISM: Artificial sequence
<220> FEATURE:
<223> OTHER INFORMATION: Primer

<400> SEQUENCE: 18
gacatcttaa gaaacattca ttgtatatgc                                     30

<210> SEQ ID NO 19
<211> LENGTH: 24
<212> TYPE: DNA
<213> ORGANISM: Artificial sequence
<220> FEATURE:
<223> OTHER INFORMATION: Primer

<400> SEQUENCE: 19
cccatttgga cgtgaatgta gaca                                           24

<210> SEQ ID NO 20
<211> LENGTH: 24
<212> TYPE: DNA
<213> ORGANISM: Artificial sequence
<220> FEATURE:
<223> OTHER INFORMATION: Primer

<400> SEQUENCE: 20
ggacgtgaat gtagacacgt cgaa                                           24

<210> SEQ ID NO 21
<211> LENGTH: 24
<212> TYPE: DNA
<213> ORGANISM: Artificial sequence
<220> FEATURE:
<223> OTHER INFORMATION: Primer

<400> SEQUENCE: 21
tcgcctataa atacgacgga tcgt                                           24

<210> SEQ ID NO 22
<211> LENGTH: 22
<212> TYPE: DNA
<213> ORGANISM: Artificial sequence
<220> FEATURE:
<223> OTHER INFORMATION: Primer

<400> SEQUENCE: 22
ctccaacctg aatgagcata cg                                             22

<210> SEQ ID NO 23
<211> LENGTH: 21
<212> TYPE: DNA
<213> ORGANISM: Artificial sequence
<220> FEATURE:
<223> OTHER INFORMATION: Primer

<400> SEQUENCE: 23
```
ctcgcaagaa ctcgcacaca c                               21

<210> SEQ ID NO 24
<211> LENGTH: 23
<212> TYPE: DNA
<213> ORGANISM: Artificial sequence
<220> FEATURE:
<223> OTHER INFORMATION: Primer

<400> SEQUENCE: 24
ggactatccc gactctcttc tca                             23

<210> SEQ ID NO 25
<211> LENGTH: 24
<212> TYPE: DNA
<213> ORGANISM: Artificial sequence
<220> FEATURE:
<223> OTHER INFORMATION: Primer

<400> SEQUENCE: 25
cacacaggga caacacacca taag                            24

<210> SEQ ID NO 26
<211> LENGTH: 23
<212> TYPE: DNA
<213> ORGANISM: Artificial sequence
<220> FEATURE:
<223> OTHER INFORMATION: Primer

<400> SEQUENCE: 26
gcagaggcat cttcaacgat gag                             23

<210> SEQ ID NO 27
<211> LENGTH: 25
<212> TYPE: DNA
<213> ORGANISM: Artificial sequence
<220> FEATURE:
<223> OTHER INFORMATION: Primer

<400> SEQUENCE: 27
ggacaacaca ccataagatc caagg                           25

<210> SEQ ID NO 28
<211> LENGTH: 21
<212> TYPE: DNA
<213> ORGANISM: Artificial sequence
<220> FEATURE:
<223> OTHER INFORMATION: Primer

<400> SEQUENCE: 28
aggcatcttc aacgatgagg c                               21

<210> SEQ ID NO 29
<211> LENGTH: 21
<212> TYPE: DNA
<213> ORGANISM: Artificial sequence
<220> FEATURE:
<223> OTHER INFORMATION: Primer

<400> SEQUENCE: 29
gtagtttggg tgggcgagag g                               21

TRANSGENIC CORN EVENT MON87403 AND METHODS FOR DETECTION THEREOF

CROSS REFERENCE TO RELATED APPLICATIONS

This application claims the benefit of U.S. Provisional Application No. 61/888,978 filed Oct. 9, 2013, herein incorporated by reference in its entirety.

INCORPORATION OF SEQUENCE LISTING

The sequence listing that is contained in the file named "MONS342USP1_ST25.txt," which is 27 kilobytes as measured in Microsoft Windows operating system and was created on Oct. 4, 2013, is filed electronically herewith and incorporated herein by reference.

FIELD

The present disclosure relates to transgenic corn event MON87403 and plants comprising the event that exhibit increased yield. The disclosure also provides cells, plant parts, seeds, plants, commodity products related to the event, and DNA molecules that are unique to the event and were created by the insertion of transgenic DNA into the genome of a corn plant. The disclosure further provides methods for detecting the presence of said corn event nucleotide sequences in a sample, probes and primers for use in detecting nucleotide sequences that are diagnostic for the presence of said corn event.

BACKGROUND

Corn is an important crop and is a primary food source in many areas of the world. The methods of biotechnology have been applied to corn for improvement of agronomic traits and the quality of the product. One such agronomic trait is increased yield.

Increased yield may be achieved in transgenic plants by the expression of a transgene capable of providing such increased yield. The expression of transgenes in plants may be influenced by many factors, such as the regulatory elements used in the transgene cassette, the chromosomal location of the transgene insert, the proximity of any endogenous regulatory elements close to the transgene insertion site, and environmental factors such as light and temperature. For example, there may be a wide variation in the overall level of transgene expression or in the spatial or temporal pattern of transgene expression between similarly-produced events. For this reason, the performance of a single given transformation event can vary. The identification of transformation events conferring beneficial characteristics can therefore represent a significant undertaking.

SUMMARY

In one aspect, the invention provides a recombinant DNA molecule comprising a nucleotide sequence selected from the group consisting of SEQ ID NO:1-8, SEQ ID NO:10, and full complements thereof. In one embodiment, the recombinant DNA molecule is formed by the junction of an inserted heterologous nucleic acid molecule and genomic DNA of a corn plant, plant cell, or seed. In another embodiment, the recombinant DNA molecule is from a transgenic corn plant comprising event MON87403, a representative sample of seed comprising said event having been deposited as ATCC Accession No. PTA-13584. In another embodiment, the recombinant DNA molecule is an amplicon diagnostic for the presence of DNA from transgenic corn event MON87403. In still another embodiment, the recombinant DNA molecule is in a corn plant, plant cell, seed, progeny plant, plant part, or commodity product. In another embodiment, the invention provides a transgenic corn plant, seed, cell, or plant part thereof comprising the recombinant DNA molecule. In other embodiments, the transgenic corn plant, seed, cell, or plant part thereof comprising the recombinant DNA molecule has increased yield, and/or the genome of such corn plant, seed, cell, or plant part thereof produces an amplicon comprising a DNA molecule selected from the group consisting of SEQ ID NO:1-8, and consecutive nucleotides of SEQ ID NO:10 when tested in a DNA amplification method. In another embodiment, the invention provides a nonliving plant material and/or a microorganism comprising the recombinant DNA molecule. In another embodiment, the microorganism comprising the recombinant DNA molecule is a plant cell.

In another aspect, the invention provides a DNA probe comprising a nucleotide sequence of sufficient length of contiguous nucleotides of SEQ ID NO:10, or a full complement thereof, to function as a DNA probe that hybridizes under stringent hybridization conditions with a DNA molecule comprising a nucleotide sequence selected from the group consisting of SEQ ID NO:1-8, and SEQ ID NO:10 and does not hybridize under the stringent hybridization conditions with a DNA molecule not comprising a nucleotide sequence selected from the group consisting of SEQ ID NO:1-8, and SEQ ID NO:10.

In another aspect, the invention provides a pair of DNA molecules comprising a first DNA molecule and a second DNA molecule different from the first DNA molecule, wherein said first and second DNA molecules each comprise a nucleotide sequence of sufficient length of contiguous nucleotides of SEQ ID NO:10, or a full complement thereof, to function as DNA primers when used together in an amplification reaction with DNA from event MON87403 to produce an amplicon diagnostic for transgenic corn event MON87403 DNA in a sample.

In still another aspect, the invention provides a method of detecting the presence of a DNA molecule from a transgenic corn plant comprising event MON87403 in a sample, said method comprising: (a) contacting said sample with the DNA probe of claim 6; (b) subjecting said sample and said DNA probe to stringent hybridization conditions; and (c) detecting hybridization of said DNA probe to a DNA molecule in said sample, wherein the hybridization of said DNA probe to said DNA molecule indicates the presence of a DNA molecule from a transgenic corn plant comprising event MON87403 in said sample.

Another aspect of the invention provides a method of detecting the presence of a DNA molecule from a transgenic corn plant comprising event MON87403 in a sample, said method comprising: (a) contacting said sample with the pair of DNA molecules of claim 7; (b) performing an amplification reaction sufficient to produce a DNA amplicon comprising a sequence selected from the group consisting of SEQ ID NO:1-8 and consecutive nucleotides of SEQ ID NO:10; and (c) detecting the presence of said DNA amplicon in said reaction, wherein the presence of said DNA amplicon in said reaction indicates the presence of a DNA molecule from a transgenic corn plant comprising event MON87403 in said sample.

In another aspect, the invention provides a DNA detection kit comprising: (a) a pair of DNA molecules comprising a first DNA molecule and a second DNA molecule different from the first DNA molecule, wherein said first and second DNA molecules each comprise a nucleotide sequence of sufficient length of contiguous nucleotides of SEQ ID NO:10, or a full complement thereof, to function as DNA primers when used together in an amplification reaction with DNA from event MON87403 to produce an amplicon diagnostic for transgenic corn event MON87403 DNA; and (b) a DNA probe comprising a nucleotide sequence of sufficient length of contiguous nucleotides of SEQ ID NO:10, or a full complement thereof, to function as a DNA probe that hybridizes under stringent hybridization conditions with a DNA molecule comprising a nucleotide sequence selected from the group consisting of SEQ ID NO:1-8 and SEQ ID NO:10 and does not hybridize under the stringent hybridization conditions with a DNA molecule not comprising a nucleotide sequence selected from the group consisting of SEQ ID NO:1-8 and SEQ ID NO:10.

Another aspect of the present invention provides a corn plant or seed, comprising event MON87403, a representative sample of seed comprising said event having been deposited under ATCC Accession No. PTA-13584. In one embodiment, the corn plant or seed is a hybrid having at least one parent comprising event MON87403.

In still another aspect, the invention provides a commodity product produced from a transgenic corn plant comprising event MON87403 and comprising the recombinant DNA molecule of claim 1, wherein detection of said nucleotide sequence in a sample derived from said commodity product is determinative that said commodity product was produced from said transgenic corn plant comprising event MON87403. In one embodiment, the commodity product is selected from the group consisting of whole or processed seeds, animal feed, oil, meal, flour, flakes, bran, biomass, and fuel products. Other embodiments of the invention provide a method of producing the commodity product, comprising: (a) obtaining a corn plant or part thereof comprising transgenic corn event MON87403; and (b) producing a corn commodity product from the corn plant or part thereof.

Another aspect of the invention provides a method of increasing yield in a crop comprising: (a) planting a crop plant or seed comprising event MON87403; and (b) growing said crop plant or seed. In one embodiment, the crop plant or seed is a corn plant or corn seed.

In another aspect, the invention provides a method of producing a corn plant with increased yield comprising: (a) sexually crossing a transgenic corn plant comprising event MON87403 comprising a nucleic acid molecule comprising a nucleotide sequence selected from the group consisting of SEQ ID NO:1-8, consecutive nucleotides of SEQ ID NO:10, and full complements thereof, with a second maize plant, thereby producing seed; (b) collecting said seed produced from said cross; (c) growing said seed to produce a plurality of progeny plants; and (d) selecting a progeny plant that has increased yield.

In another aspect, the invention provides a method of producing a corn plant with increased yield comprising: (a) selfing a transgenic corn plant comprising event MON87403 comprising a nucleic acid molecule comprising a nucleotide sequence selected from the group consisting of SEQ ID NO:1-8, and consecutive nucleotides of SEQ ID NO:10, thereby producing seed; (b) collecting said seed produced from said selfing; (c) growing said seed to produce a plurality of progeny plants; and (d) selecting a progeny plant that has increased yield.

Another aspect of the invention provides a method of producing hybrid corn seed comprising: (a) planting transgenic corn seed comprising event MON87403 in an area; (b) growing a corn plant from said seed; (c) fertilizing said corn plant with pollen from a second parent corn plant; and (d) harvesting seed from said corn plant, wherein said seed is hybrid corn seed produced by the cross of a transgenic corn plant comprising event MON87403 with a second parent plant. In one embodiment, the method further comprising planting a second parent corn plant seed in said area and growing a corn plant from said second parent corn plant. In another embodiment, the said second parent corn plant has increased yield.

In another aspect, the invention provides a method of determining the zygosity of a corn plant genome comprising corn event MON87403 DNA in a sample comprising: (a) contacting the sample with a first pair of DNA molecules and a second distinct pair of DNA molecules that: (i) when used together in a nucleic acid amplification reaction with corn event MON87403 DNA, produces a first amplicon that is diagnostic for corn event MON87403; and (ii) when used together in a nucleic acid amplification reaction with corn genomic DNA other than MON87403 DNA, produces a second amplicon that is diagnostic for corn wild type genomic DNA other than event MON87403 DNA; (b) performing a nucleic acid amplification reaction; and (c) detecting said first amplicon and said second amplicon; wherein the presence of said first and second amplicons is diagnostic of a heterozygous genome in said sample, and wherein the presence of only said first amplicon is diagnostic of a genome homozygous for corn event MON87403 in said sample. In an embodiment, the first set of DNA molecules comprises SEQ ID NO:11 and SEQ ID NO:12, and the second set of DNA molecules comprises SEQ ID NO:14 and SEQ ID NO:15.

BRIEF DESCRIPTION OF THE SEQUENCES

Figure 1:
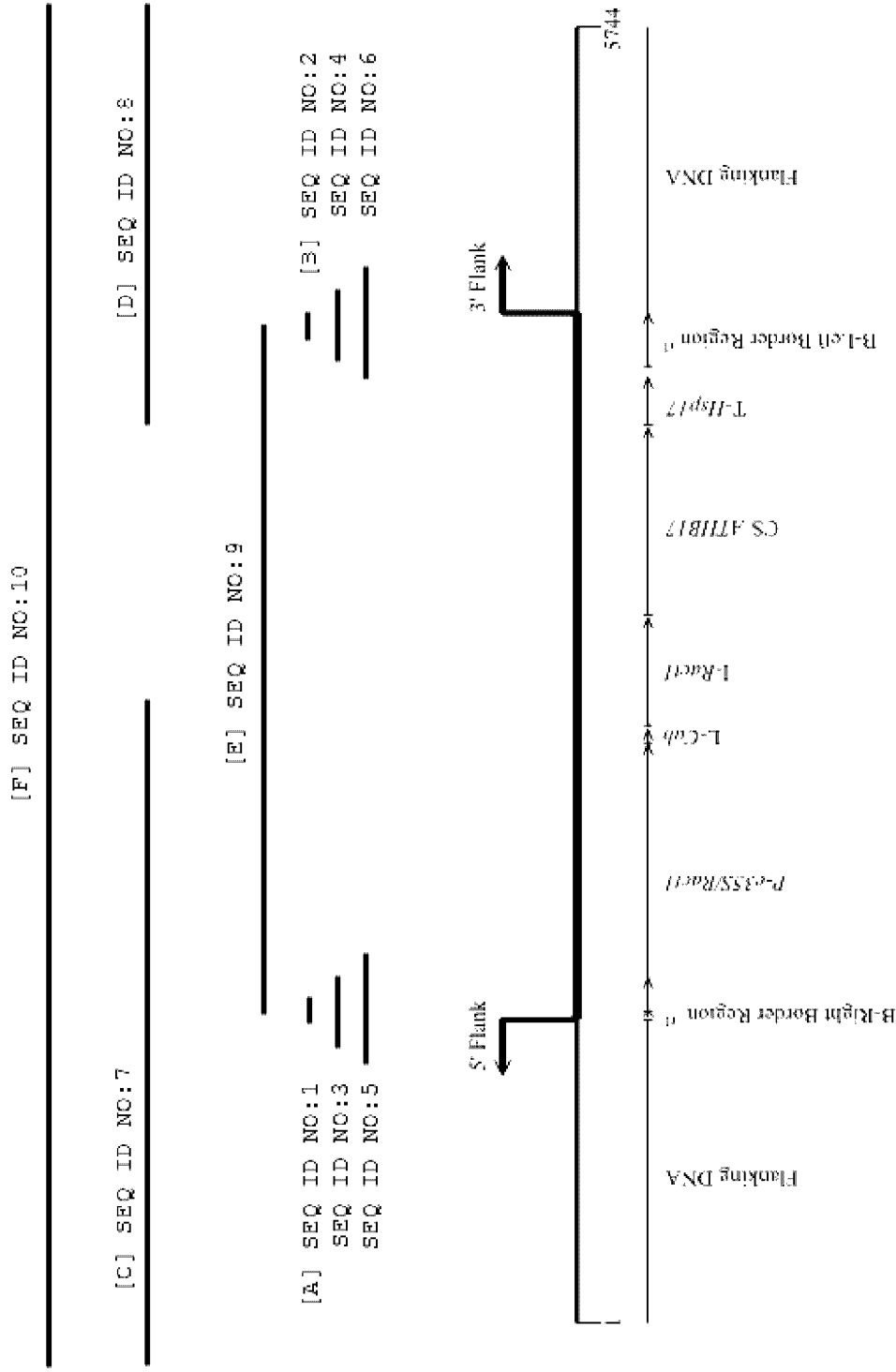
FIG. 1—Shows a diagrammatical representation of the transgenic insert in the genome of a corn comprising event MON87403; [A] corresponds to the relative positions of SEQ ID NOs:1, 3, and 5, all of which form the junction between the 5' portion of the transgenic insert and the 3' portion of the flanking genomic DNA; [B] corresponds to the relative positions of SEQ ID NOs:2, 4, and 6, all of which form the junction between the 3' portion of the transgenic insert and the 5' portion of the flanking genomic DNA; [C] corresponds to the relative position of SEQ ID NO:7, which contains the corn genomic flanking region and a portion of the arbitrarily designated 5' end of the transgenic DNA insert; [D] corresponds to the relative position of SEQ ID NO:8, which contains the corn genome flanking region and a portion of the arbitrarily designated 3' end of the transgenic DNA insert; [E] represents SEQ ID NO:9, which is the sequence of the transgenic DNA insert including the ATHB17 expression cassette integrated into the genome of a corn plant comprising event MON87403; [F] represents SEQ ID NO:10, which is the contiguous sequence comprising the 5' flanking genomic sequence, the transgenic insert and the 3' flanking genomic sequence, comprising, as represented in the figure from left to right, SEQ ID NO:7, SEQ ID NO:9, and SEQ ID NO:8, in which SEQ ID NOs:1, 3, and 5, and SEQ ID NOs:2, 4, and 6 are incorporated as set forth above, as these sequences are present in the genome of a plant comprising event MON87403.

SEQ ID NO:1 is a 20 nucleotide sequence representing the 5' junction region of a maize genomic DNA and an integrated transgenic expression cassette (positions 1336 through 1355 of SEQ ID NO:10).

SEQ ID NO:2 is a 20 nucleotide sequence representing the 3' junction region of a maize genomic DNA and an integrated transgenic expression cassette (positions 4468 through 4487 of SEQ ID NO:10).

SEQ ID NO:3 is a 60 nucleotide sequence representing the 5' junction region of a maize genomic DNA and an integrated transgenic expression cassette (positions 1316 through 1375 of SEQ ID NO:10).

SEQ ID NO:4 is a 60 nucleotide sequence representing the 3' junction region of a maize genomic DNA and an integrated transgenic expression cassette (positions 4448 through 4507 of SEQ ID NO:10).

SEQ ID NO:5 is a 100 nucleotide sequence representing the 5' junction region of a maize genomic DNA and an integrated transgenic expression cassette (positions 1296 through 1395 of SEQ ID NO:10).

SEQ ID NO:6 is a 100 nucleotide sequence representing the 3' junction region of a maize genomic DNA and an integrated transgenic expression cassette (positions 4428 through 4527 of SEQ ID NO:10).

SEQ ID NO:7 is a 3000 nucleotide 5' sequence flanking the inserted DNA of MON87403 up to and including a region of transgene DNA insertion (positions 1 through 3000 of SEQ ID NO:10).

SEQ ID NO:8 is a 2624 nucleotide 3' sequence flanking the inserted DNA of MON87403 up to and including a region of transgene DNA insertion (positions 3121 through 5744 of SEQ ID NO:10).

SEQ ID NO:9 is the sequence fully integrated into the maize genomic DNA and containing the expression cassette DNA (positions 1346 through 4477 of SEQ ID NO:10).

SEQ ID NO:10 is the nucleotide sequence representing the contig of the 5' sequence flanking the inserted DNA of MON87403 (SEQ ID NO:7), the sequence fully integrated into the corn genomic DNA and containing the expression cassette (SEQ ID NO:9), and the 3' sequence flanking the inserted DNA of MON87403 (SEQ ID NO:8) and includes SEQ ID NOs:1-6.

SEQ ID NO:11 is a transgene-specific assay primer SQ23846 used to identify event MON87403. A PCR amplicon produced from a TAQMAN® (PE Applied Biosystems, Foster City, Calif.) assay using the combination of primers SEQ ID NO:11 and SEQ ID NO:12 is a positive result for the presence of the event MON87403.

SEQ ID NO:12 is a transgene-specific assay primer SQ4603 used to identify event MON87403.

SEQ ID NO:13 is a transgene-specific assay 6-FAM-labeled probe PB10644 used to identify MON87403. This probe is a 6FAM™-labeled synthetic oligonucleotide. Release of a fluorescent signal in an amplification reaction using primers SEQ ID NO:11-12 in combination with the 6FAM™-labeled probe is diagnostic of event MON87403 in a TAQMAN® assay.

SEQ ID NO:14 is a transgene-specific assay internal control primer SQ25061.

SEQ ID NO:15 is a transgene-specific assay internal control primer SQ25062.

SEQ ID NO:16 is a transgene-specific assay internal control VIC™-labeled PB10866.

SEQ ID NO:17 is a transgene-specific forward primer AS349 for PCR used to identify MON87403.

SEQ ID NO:18 is a transgene-specific reverse primer AS350 for PCR used to identify MON87403.

SEQ ID NO:19 is primer SQ6164, used to detect the 5' (left) junction region of event MON87403.

SEQ ID NO:20 is primer SQ13205, used in PCR to detect the 5' (left) junction region of event MON87403.

SEQ ID NO:21 is primer SQ6165, used to detect the 5' (left) junction region of event MON87403.

SEQ ID NO:22 is primer SQ22458, used to detect the 5' (left) junction region of event MON87403.

SEQ ID NO:23 is primer SQ22459, used to detect the 5' (left) junction region of event MON87403.

SEQ ID NO:24 is primer SQ21173, used to detect the 3' (right) junction region of event MON87403.

SEQ ID NO:25 is primer SQ22464, used to detect the 3' (right) junction region of event MON87403.

SEQ ID NO:26 is primer SQ22460, used to detect the 3' (right) junction region of event MON87403.

SEQ ID NO:27 is primer SQ22465, used to detect the 3' (right) junction region of event MON87403.

SEQ ID NO:28 is primer SQ22461, used to detect the 3' (right) junction region of event MON87403.

SEQ ID NO:29 is primer SQ22471, used to detect the 3' (right) junction region of event MON87403.

DETAILED DESCRIPTION

The following definitions and methods are provided to better define the present disclosure and to guide those of ordinary skill in the art in the practice of the present disclosure. Unless otherwise noted, terms are to be understood according to conventional usage by those of ordinary skill in the relevant art. Definitions of common terms in molecular biology may also be found in Rieger et al., *Glossary of Genetics: Classical and Molecular*, 5th edition, Springer-Verlag: New York, 1991; and Lewin, Genes V, Oxford University Press: New York, 1994.

The present disclosure provides transgenic corn event MON87403 (also referred to herein as MON87403). The term "event" as used herein refers to DNA molecules produced as a result of inserting transgenic DNA into a plant's genome at a particular location on a chromosome. Event MON87403 refers to the DNA molecules produced as a result of the insertion of transgenic DNA having a sequence provided herein as SEQ ID NO:9 into a particular chromosomal location in the *Zea mays* genome. Plants, seeds, progeny, cells, and plant parts thereof comprising event MON87403 are also provided in the present disclosure. Plants comprising MON87403 exhibit increased grain yield.

As used herein, the term "corn" or "maize" means *Zea mays* and includes all plant varieties that can be bred with maize, including wild maize species as well as those plants belonging to *Zea* that permit breeding between species.

A transgenic "event" is produced by transformation of plant cells with heterologous DNA, i.e., a nucleic acid construct that comprises a transgene of interest, regeneration of a population of independently transformed transgenic plants resulting from the insertion of the transgene into the genome of the plants, and selection of a particular plant with desirable molecular characteristics, such as insertion of a single copy of the transgene into a particular genome location, integrity of the transgenic DNA, and an enhanced trait such as increased grain yield. A plant comprising the event can refer to the original transformant that includes the transgene inserted into the particular location in the plant's genome. A plant comprising the event can also refer to progeny of the original transformant that retain the transgene at the same particular location in the plant's genome. Such progeny may be produced by selfing, or by a sexual outcross with a different plant comprising the same event, or its progeny, and another plant. Such another plant may be a transgenic plant comprising the same or a different transgene; or may be a non-transgenic plant, such as one from a different variety. The resulting progeny may be homozygous or heterozygous for event MON87403 DNA (inserted DNA and flanking DNA). Even after repeated back-crossing to a recurrent parent, the event DNA from the transformed parent is present in the progeny of the cross at the same genomic location.

A DNA molecule comprising event MON87403 refers to a DNA molecule comprising at least a portion of the inserted transgenic DNA (provided as SEQ ID NO:9) and at least a portion of the flanking genomic DNA immediately adjacent to the inserted DNA. As such, a DNA molecule comprising event MON87403 has a nucleotide sequence representing at least a portion of the transgenic DNA insert and at least a portion of the particular region of the genome of the plant into which the transgenic DNA was inserted. The arrangement of the inserted DNA in event MON87403 in relation to the surrounding plant genome is specific and unique to event MON87403 and as such the nucleotide sequence of such a DNA molecule is diagnostic and identifying for event MON87403. Examples of the sequence of such a DNA molecule are provided herein as SEQ ID NOs:1-8 and SEQ ID NO:10. Such a DNA molecule is also an integral part of the chromosome of a plant that comprises event MON87403 and may be passed on to progeny of the plant.

As used herein, a "recombinant DNA molecule" is a DNA molecule comprising a combination of DNA molecules that would not naturally occur together and is the result of human intervention, e.g., a DNA molecule that is comprised of a combination of at least two DNA molecules heterologous to each other, and/or a DNA molecule that is artificially synthesized and comprises a polynucleotide sequence that deviates from the polynucleotide sequence that would normally exist in nature, and/or a DNA molecule that comprises a transgene incorporated into a host cell's genomic DNA and the associated flanking DNA of the host cell's genome. An example of a recombinant DNA molecule is a DNA molecule described herein resulting from the insertion of the transgene into the Zea mays genome, which may ultimately result in the expression of a recombinant RNA and/or protein molecule in that organism. The nucleotide sequence or any fragment derived therefrom would also be considered a recombinant DNA molecule if the DNA molecule can be extracted from cells, or tissues, or homogenate from a plant or seed or plant tissue; or can be produced as an amplicon from extracted DNA or RNA from cells, or tissues, or homogenate from a plant or seed or plant tissue, any of which is derived from such materials derived from a plant comprising event MON87403. For that matter, the junction sequences as set forth at SEQ ID NOs:1-6, and nucleotide sequences derived from event MON87403 that also contain these junction sequences are defined herein to be recombinant DNA, whether these sequences are present within the genome of the cells comprising event MON87403 or present in detectable amounts in tissues, progeny, biological samples or commodity products derived from plants comprising event MON87403. As used herein, the term "transgene" refers to a polynucleotide molecule incorporated into a host cell's genome. Such transgene may be heterologous to the host cell. The term "transgenic plant" refers to a plant comprising such a transgene. A "transgenic plant" includes a plant, plant part, a plant cell or seed whose genome has been altered by the stable integration of recombinant DNA. A transgenic plant includes a plant regenerated from an originally-transformed plant cell and progeny transgenic plants from later generations or crosses of a transformed plant. As a result of such genomic alteration, the transgenic plant is distinctly different from the related wild type plant. An example of a transgenic plant is a plant described herein as comprising event MON87403.

As used herein, the term "heterologous" refers to a sequence that is not normally present in a given host genome in the genetic context in which the sequence is currently found. In this respect, the sequence may be native to the host genome, but be rearranged with respect to other genetic sequences within the host sequence.

The present disclosure provides DNA molecules and their corresponding nucleotide sequences. As used herein, the terms "DNA sequence," "nucleotide sequence," and "polynucleotide sequence" refer to the sequence of nucleotides of a DNA molecule, usually presented from the 5' (upstream or left) end to the 3' (downstream or right) end. The nomenclature used herein is that required by Title 37 of the United States Code of Federal Regulations §1.822 and set forth in the tables in WIPO Standard ST.25 (1998), Appendix 2, Tables 1 and 3. The present disclosure is disclosed with reference to only one strand of the two nucleotide sequence strands that are provided in transgenic event MON87403. Therefore, by implication and derivation, the complementary sequences, also referred to in the art as the complete complement or the reverse complementary sequences, are within the scope of the present disclosure and are therefore also intended to be within the scope of the subject matter claimed.

The nucleotide sequence corresponding to the complete nucleotide sequence of the inserted transgenic DNA and substantial segments of the Zea mays genomic DNA flanking either end of the inserted transgenic DNA is provided herein as SEQ ID NO:10. A subsection of this is the inserted transgenic DNA provided as SEQ ID NO:9. The nucleotide sequence of the genomic DNA flanking the 5' end of the inserted transgenic DNA and a portion of the 5' end of the inserted DNA is provided herein as SEQ ID NO:7. The nucleotide sequence of the genomic DNA flanking the 3' end of the inserted transgenic DNA and a portion of the 3' end of the inserted DNA is provided herein as SEQ ID NO:8. The region spanning the location where the transgenic DNA connects to and is linked to the genomic DNA is referred to herein as the junction. A "junction sequence" or "junction region" refers to a DNA sequence and/or corresponding DNA molecule that spans the inserted transgenic DNA and the adjacent flanking genomic DNA. Examples of a junction sequence of event MON87403 are provided herein as SEQ ID NOs:1-6. The identification of one of these junction sequences in a nucleotide molecule derived from a corn plant or seed is conclusive that the DNA was obtained from event MON87403 and is diagnostic for the presence of DNA from event MON87403. SEQ ID NO:1 is a 20 bp nucleotide sequence spanning the junction between the genomic DNA and the 5' end of the inserted DNA. SEQ ID NO:3 is a 60 bp nucleotide sequence spanning the junction between the genomic DNA and the 5' end of the inserted DNA. SEQ ID NO:5 is a 100 bp nucleotide sequence spanning the junction between the genomic DNA and the 5' end of the inserted DNA. SEQ ID NO:2 is a 20 bp nucleotide sequence spanning the junction between the genomic DNA and the 3' end of the inserted DNA. SEQ ID NO:4 is a 60 bp nucleotide sequence spanning the junction between the genomic DNA and the 3' end of the inserted DNA. SEQ ID NO:6 is a 100 bp nucleotide sequence spanning the junction between the genomic DNA and the 3' end of the inserted DNA. Any segment of DNA derived from transgenic event MON87403 that includes at least 19 consecutive nucleotides of SEQ ID NO:1, or 31, 32, 33, 34, 35, 40, 45, 50, 55, or all consecutive nucleotides of SEQ ID NO:3, or 51, 52, 53, 54, 55, 60, 65, 70, 75, 80, 85, 90, 95, or all consecutive nucleotides of SEQ ID NO:5 is within the scope of the present disclosure. Any segment of DNA derived from transgenic event MON87403 that includes at least 18 consecutive nucleotides of SEQ ID NO:2, or 31, 32, 33, 34, 35, 40, 45, 50, 55, or all consecutive nucleotides of SEQ ID NO:4, or 51, 52, 53, 54, 55, 60, 65, 70, 75, 80, 85, 90, 95, or all consecutive nucleotides of SEQ ID NO:6 is within the scope of the present disclosure. In addition, any polynucleotide molecule comprising a sequence complementary to any of the sequences described within this paragraph is within the scope of the present disclosure. FIG. 1 is an illustration of the transgenic DNA insert in the genome of a corn plant comprising event MON87403, and the relative positions of SEQ ID NOs: 1-10 arranged 5' to 3'. The present disclosure also provides a nucleic acid molecule comprising a polynucleotide having a sequence that is at least 90%, 91%, 92%, 93%, 94%, 95%, 96%, 97%, 98%, or 99% identical to the full-length of SEQ ID NO:10.

The present disclosure further provides exemplary DNA molecules that can be used either as primers or probes for diagnosing the presence of DNA derived from event MON87403 in a sample. Such primers or probes are specific for a target nucleic acid sequence and as such are useful for the identification of event MON87403 nucleic acid sequence by the methods of the disclosure described herein.

A "probe" is an isolated nucleic acid to which is attached a detectable label or reporter molecule, e.g., a radioactive isotope, ligand, chemiluminescent agent, or enzyme. Such a probe is complementary to a strand of a target nucleic acid. In the case of the present disclosure, such a probe is complementary to a strand of genomic DNA from a corn comprising event MON87403, whether from a corn plant or from a sample that comprises DNA from the event. Probes according to the present disclosure include not only deoxyribonucleic or ribonucleic acids but also polyamides and other probe materials that bind specifically to a target DNA sequence. The detection of such binding can be used to diagnose/determine/confirm the presence of that target DNA sequence in a particular sample.

A "primer" is typically an isolated polynucleotide that is designed for use in specific annealing or hybridization methods to hybridize to a complementary target DNA strand to form a hybrid between the primer and the target DNA strand, and then extended along the target DNA strand by a polymerase, e.g., a DNA polymerase. A pair of primers may be used with template DNA, such as a sample of Zea mays genomic DNA, in a thermal or isothermal amplification, such as polymerase chain reaction (PCR), or other nucleic acid amplification methods, to produce an amplicon, where the amplicon produced from such reaction would have a DNA sequence corresponding to sequence of the template DNA located between the two sites where the primers hybridized to the template. As used herein, an "amplicon" is a piece or fragment of DNA that has been synthesized using amplification techniques, i.e. the product of an amplification reaction. In one embodiment of the disclosure, an amplicon diagnostic for event MON87403 comprises a sequence not naturally found in the Zea mays genome. Primer pairs, as used in the present disclosure, are intended to refer to use of two primers binding opposite strands of a double stranded nucleotide segment for the purpose of amplifying linearly the polynucleotide segment between the positions targeted for binding by the individual members of the primer pair, typically in a thermal or isothermal amplification reaction or other nucleic acid amplification methods. In embodiments, exemplary DNA molecules useful as primers are provided as SEQ ID NOs:11-12, 14-15, 17-18, and 19-29. For example, exemplary event-specific primers for PCR to identify event MON87403 are provided as SEQ ID NOs:17-18. Exemplary primers that may be used for analysis of the 5' (left) junction region are provided as SEQ ID NOs:19-23, and exemplary primers that may be used for analysis of the 3' (right) junction region are provided as SEQ ID NOs:24-29. Exemplary primers that may be used for zygosity testing for event MON87403 are provided as SEQ ID NOs:11-12 and SEQ ID NOs: 14-15. The use of the term "amplicon" specifically excludes primer-dimers that may be formed in the DNA amplification reaction.

Probes and primers according to the present disclosure may have complete sequence identity to the target sequence, although primers and probes differing from the target sequence that retain the ability to hybridize preferentially to target sequences may be designed by conventional methods. In order for a nucleic acid molecule to serve as a primer or probe it needs only be sufficiently complementary in sequence to be able to form a stable double-stranded structure under the particular solvent and salt concentrations employed. Any nucleic acid hybridization or amplification method can be used to identify the presence of transgenic DNA from event MON87403 in a sample. Probes and primers are generally at least about 11 nucleotides, at least about 18 nucleotides, at least about 24 nucleotides, and at least about 30 nucleotides or more in length. Such probes and primers hybridize specifically to a target sequence under high stringency hybridization conditions.

Methods for preparing and using probes and primers are described, for example, in *Molecular Cloning: A Laboratory Manual,* 2nd ed., vol. 1-3, ed. Sambrook et al., Cold Spring Harbor Laboratory Press, Cold Spring Harbor, N.Y., 1989 (hereinafter, "Sambrook et al., 1989"); *Current Protocols in Molecular Biology*, ed. Ausubel et al., Greene Publishing and Wiley-Interscience, New York, 1992 (with periodic updates); and Innis et al., *PCR Protocols: A Guide to Methods and Applications*, Academic Press: San Diego, 1990. PCR-primer pairs can be derived from a known sequence, for example, by using computer programs intended for that purpose such as Primer (Version 0.5, © 1991, Whitehead Institute for Biomedical Research, Cambridge, Mass.).

Primers and probes based on the flanking DNA and insert sequences disclosed herein can be used to confirm the disclosed sequences by known methods, e.g., by re-cloning and sequencing such sequences.

The nucleic acid probes and primers of the present disclosure hybridize under stringent conditions to a target DNA sequence. Any nucleic acid hybridization or amplification method can be used to identify the presence of DNA from a transgenic event in a sample. Nucleic acid molecules or fragments thereof are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least "low-stringency" conditions. Similarly, the molecules are said to be "complementary" if they can hybridize to one another with sufficient stability to permit them to remain annealed to one another under "high-stringency" conditions. Stringency conditions are described by Sambrook et al., 1989, and by Haymes et al., In: *Nucleic Acid Hybridization, A Practical Approach*, IRL Press, Washington, D.C. (1985). Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

As used herein, a substantially homologous sequence is a nucleic acid sequence that will specifically hybridize to the complement of the nucleic acid sequence to which it is being compared under high stringency conditions. Appropriate stringency conditions that promote DNA hybridization, for example, 6.0× sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. In one embodiment, a nucleic acid of the present disclosure will specifically hybridize to one or more of the nucleic acid molecules set forth in SEQ ID NOs:1-6, or complements or fragments thereof under high stringency conditions. The hybridization of the probe to the target DNA molecule can be detected by any number of methods known to those skilled in the art. These can include, but are not limited to, fluorescent tags, radioactive tags, antibody based tags, and chemiluminescent tags.

Regarding the amplification of a target nucleic acid sequence (e.g., by PCR) using a particular amplification primer pair, "stringent conditions" are conditions that permit the primer pair to hybridize only to the target nucleic acid sequence to which a primer having the corresponding wild-type sequence (or its complement) would bind and preferably to produce a unique amplification product, the amplicon, in a DNA amplification reaction. Examples of DNA amplification methods include PCR, Recombinase Polymerase Amplification (RPA) (see for example U.S. Pat. No. 7,485,428), Strand Displacement Amplification (SDA) (see for example, U.S. Pat. Nos. 5,455,166 and 5,470,723), Transcription-Mediated Amplification (TMA) (see for example, Guatelli et al., *Proc. Natl. Acad. Sci. USA* 87:1874-1878, 1990), Rolling Circle Amplification (RCA) (see for example, Fire and Xu, *Proc. Natl. Acad Sci. USA* 92:4641-4645, 1995; Lui, et al., *J. Am. Chem. Soc.* 118:1587-1594, 1996; Lizardi, et al., *Nature Genetics* 19:225-232, 1998; U.S. Pat. Nos. 5,714,320 and 6,235,502), Helicase Dependent Amplification (HDA) (see for example Vincent et al., *EMBO Reports* 5(8): 795-800, 2004; U.S. Pat. No. 7,282, 328), and Multiple Displacement Amplification (MDA) (see for example Dean et al., *Proc. Natl. Acad Sci. USA* 99:5261-5266, 2002).

The term "specific for (a target sequence)" indicates that a probe or primer hybridizes under stringent hybridization conditions only to the target sequence in a sample comprising the target sequence.

As used herein, the term "isolated" refers to at least partially separating a molecule from other molecules normally associated with it in its native or natural state. In one embodiment, the term "isolated" refers to a DNA molecule that is at least partially separated from the nucleic acids that normally flank the DNA molecule in its native or natural state. DNA molecules fused to regulatory or coding sequences with which they are not normally associated, for example as the result of recombinant techniques, are considered isolated herein. Thus, any transgenic, recombinant, chimeric or artificial nucleotide sequence would be considered to be an isolated nucleotide sequence since these are not naturally occurring sequences. A transgenic, recombinant, chimeric or artificial nucleotide sequence would be considered to be an isolated nucleotide sequence whether it is present within the plasmid, vector or construct used to transform plant cells, within the genome of the plant, or is present in detectable amounts in tissues, progeny, biological samples or commodity products derived from the plant. The nucleotide sequence or any fragment derived therefrom would therefore be considered to be isolated or isolatable if the DNA molecule can be extracted from cells, or tissues, or homogenate from a plant or seed or plant organ; or can be produced as an amplicon from extracted DNA or RNA from cells, or tissues, or homogenate from a plant or seed or plant organ, any of which is derived from such materials derived from the transgenically altered plant.

Any number of methods well known to those skilled in the art can be used to isolate and manipulate a DNA molecule, or fragment thereof, disclosed in the present disclosure. For example, PCR (polymerase chain reaction) technology can be used to amplify a particular starting DNA molecule and/or to produce variants of the original molecule. DNA molecules, or fragments thereof, can also be obtained by other techniques such as by directly synthesizing the fragment by chemical means, as is commonly practiced by using an automated oligonucleotide synthesizer.

It would be advantageous to be able to detect the presence of transgene/genomic DNA of a particular plant in order to determine whether progeny of a self-pollination or sexual cross contain the transgene/genomic DNA of interest. In addition, a method for detecting a particular transgenic plant is helpful when complying with regulations requiring the pre-market approval and labeling of foods derived from the transgenic crop plants.

The presence of a transgene may be detected by any well known nucleic acid detection method such as the polymerase chain reaction (PCR) or DNA hybridization using nucleic acid probes. These detection methods generally focus on frequently used genetic elements, such as promoters, terminators, marker genes, etc. As a result, such methods may not be useful for discriminating between different transformation events, particularly those produced using the same DNA construct unless the sequence of chromosomal DNA adjacent to the inserted DNA ("flanking DNA") is known. An event-specific PCR assay is discussed, for example, by Taverniers et al. (*J. Agric. Food Chem.*, 53:3041-3052, 2005) in which an event-specific tracing system for transgenic maize lines Bt11, Bt176, and GA21 and for canola event GT73 was demonstrated. In this study, event-specific primers and probes were designed based upon the sequences of the genome/transgene junctions for each event. Transgenic plant event specific DNA detection methods have also been described in U.S. Pat. Nos. 6,893,826; 6,825,400; 6,740,488; 6,733,974; 6,689,880; 6,900,014; and 6,818,807.

The DNA molecules and corresponding nucleotide sequences provided herein are therefore useful for, among other things, identifying event MON87403, selecting plant varieties or hybrids comprising event MON87403, detecting the presence of DNA derived from event MON87403 in a sample, and monitoring samples for the presence and/or absence of event MON87403 or plants and plant parts comprising event MON87403.

The present disclosure provides plants, progeny, seeds, plant cells, plant parts (such as pollen, ovule, flower, root or stem tissue, fibers, and leaves), and commodity products. These plants, progeny, seeds, plant cells, plant parts, and commodity products contain a detectable amount of a polynucleotide of the present disclosure, such as a polynucleotide comprising at least one of the sequences provided as at least 19 consecutive nucleotides of SEQ ID NO:1, at least 18 consecutive nucleotides of SEQ ID NO:2, at least 31 consecutive nucleotides of SEQ ID NO:3, at least 31 consecutive nucleotides of SEQ ID NO:4, at least 51 consecutive nucleotides of SEQ ID NO:5, or at least 51 consecutive nucleotides of SEQ ID NO:6. Plants, progeny, seeds, plant cells, plant parts and commodity products of the present disclosure may also contain one or more additional transgenes. Such transgene may be any nucleotide sequence encoding a protein or RNA molecule conferring a desirable trait including but not limited to increased insect resistance, increased water use efficiency or drought tolerance, increased yield performance, increased yield potential, increased nitrogen use efficiency or increase tolerance to nitrogen stress such as high or low nitrogen supply, increased seed quality, increased disease resistance, improved nutritional quality, and/or increased herbicide tolerance, such as glyphosate or dicamba tolerance, in which the desirable trait is measured with respect to a comparable plant lacking such additional transgene.

The present disclosure provides plants, progeny, seeds, plant cells, and plant part such as pollen, ovule kernel, flower, root or stem tissue, and leaf derived from a transgenic plant comprising event MON87403. A representative sample of seed comprising event MON87403 has been deposited according to the Budapest Treaty for the purpose of enabling the present disclosure. The repository selected for receiving the deposit is the American Type Culture Collection (ATCC) having an address at 10801 University Boulevard, Manassas, Va. USA, Zip Code 20110. The ATCC repository has assigned the accession No. PTA-13584 to event MON87403-containing seed.

The present disclosure provides a microorganism comprising a DNA molecule having a nucleotide sequence selected from the group consisting of at least 19 consecutive nucleotides of SEQ ID NO:1, at least 18 consecutive nucleotides of SEQ ID NO:2, at least 31 consecutive nucleotides of SEQ ID NO:3, at least 31 consecutive nucleotides of SEQ ID NO:4, at least 51 consecutive nucleotides of SEQ ID NO:5, or at least 51 consecutive nucleotides of SEQ ID NO:6 present in its genome. An example of such a microorganism is a transgenic plant cell. Microorganisms, such as a plant cell of the present disclosure, are useful in many industrial applications, including but not limited to: (i) use as research tool for scientific inquiry or industrial research; (ii) use in culture for producing endogenous or recombinant carbohydrate, lipid, nucleic acid, enzymes or protein products or small molecules that may be used for subsequent scientific research or as industrial products; and (iii) use with modern plant tissue culture techniques to produce transgenic plants or plant tissue cultures that may then be used for agricultural research or production. The production and use of microorganisms such as transgenic plant cells utilizes modern microbiological techniques and human intervention to produce a man-made, unique microorganism. In this process, a recombinant DNA is inserted into a plant cell's genome to create a transgenic plant cell that is separate and unique from naturally occurring plant cells. This transgenic plant cell can then be cultured much like bacteria and yeast cells using modern microbiology techniques and may exist in an undifferentiated, unicellular state. The new plant cell's genetic composition and phenotype is a technical effect created by the integration of a heterologous DNA into the genome of the cell. Another aspect of the present disclosure is a method of using a microorganism of the present disclosure. Methods of using microorganisms of the present disclosure, such as transgenic plant cells, include (i) methods of producing transgenic cells by integrating a recombinant DNA into genome of the cell and then using this cell to derive additional cells possessing the same heterologous DNA; (ii) methods of culturing cells that contain recombinant DNA using modern microbiology techniques; (iii) methods of producing and purifying endogenous or recombinant carbohydrate, lipid, nucleic acid, enzymes or protein products from cultured cells; and (iv) methods of using modern plant tissue culture techniques with transgenic plant cells to produce transgenic plants or transgenic plant tissue cultures.

As used herein, "progeny" includes any plant, seed, plant cell, and/or regenerable plant part comprising the event DNA derived from an ancestor plant and/or a polynucleotide having at least one of the sequences provided as at least 19 consecutive nucleotides of SEQ ID NO:1, at least 18 consecutive nucleotides of SEQ ID NO:2, at least 31 consecutive nucleotides of SEQ ID NO:3, at least 31 consecutive nucleotides of SEQ ID NO:4, at least 51 consecutive nucleotides of SEQ ID NO:5, or at least 51 consecutive nucleotides of SEQ ID NO:6. Plants, progeny, and seeds may be homozygous or heterozygous for the MON87403 event DNA. Progeny may be grown from seeds produced by a plant comprising event MON87403 and/or from seeds produced by a plant fertilized with pollen or ovule from a plant comprising event MON87403.

Progeny plants may be self-pollinated (also known as "selfing") to generate a true breeding line of plants, i.e., plants homozygous for the MON87403 event DNA. Alternatively, progeny plants may be outcrossed, i.e., bred with another plant, to produce a varietal or a hybrid seed or plant. The other plant may be transgenic or nontransgenic. A varietal or hybrid seed or plant of the present disclosure may thus be derived by crossing a first parent that lacks the specific and unique DNA of event MON87403 with a second parent comprising event MON87403, resulting in a hybrid comprising the specific and unique DNA of event MON87403. Each parent can be a hybrid or an inbred/variety, so long as the cross or breeding results in a plant or seed of the present disclosure, i.e., a seed having at least one allele comprising the specific and unique DNA of event MON87403 and/or at least 19 consecutive nucleotides of SEQ ID NO:1, at least 19 consecutive nucleotides of SEQ ID NO:2, at least 31 consecutive nucleotides of SEQ ID NO:3, at least 31 consecutive nucleotides of SEQ ID NO:4, at least 51 consecutive nucleotides of SEQ ID NO:5, or at least 51 consecutive nucleotides of SEQ ID NO:6. Two different transgenic plants may thus be mated to produce hybrid offspring that contain two independently segregating, added, transgenes. For example, a plant comprising event MON87403 with increased yield can be crossed with another transgenic plant, such as one tolerant to glyphosate, to produce a plant having the characteristics of both transgenic parents. Selfing of appropriate progeny can produce plants that are homozygous for both added transgenes. Back-crossing to a parental plant and out-crossing with a non-transgenic plant are also contemplated, as is vegetative propagation. Descriptions of other breeding methods that are commonly used for different traits and crops can be found in one of several references, e.g., Fehr, in *Breeding Methods for Cultivar Development*, Wilcox J. ed., American Society of Agronomy, Madison Wis. (1987). Sexually crossing one plant with another plant, i.e., cross-pollinating, may be accomplished or facilitated by human intervention, for example: by human hands collecting the pollen of one plant and contacting this pollen with the style or stigma of a second plant; by human hands and/or human actions removing, destroying, or covering the stamen or anthers of a plant (e.g., by manual intervention or by application of a chemical gametocide) so that natural self-pollination is prevented and cross-pollination would have to take place in order for fertilization to occur; by human placement of pollinating insects in a position for "directed pollination" (e.g., by placing beehives in orchards or fields or by caging plants with pollinating insects); by human opening or removing of parts of the flower to allow for placement or contact of foreign pollen on the style or stigma; by selective placement of plants (e.g., intentionally planting plants in pollinating proximity); and/or by application of chemicals to precipitate flowering or to foster receptivity (of the stigma for pollen).

In practicing this method, the step of sexually crossing one plant with itself, i.e., self-pollinating or selfing, may be accomplished or facilitated by human intervention, for example: by human hands collecting the pollen of the plant and contacting this pollen with the style or stigma of the same plant and then optionally preventing further fertilization of the plant; by human hands and/or actions removing, destroying, or covering the stamen or anthers of other nearby plants (e.g., by detasseling or by application of a chemical gametocide) so that natural cross-pollination is prevented and self-pollination would have to take place in order for fertilization to occur; by human placement of pollinating insects in a position for "directed pollination" (e.g., by caging a plant alone with pollinating insects); by human manipulation of the flower or its parts to allow for self-pollination; by selective placement of plants (e.g., intentionally planting plants beyond pollinating proximity); and/or by application of chemicals to precipitate flowering or to foster receptivity (of the stigma for pollen).

The present disclosure provides a plant part that is derived from a plant comprising event MON87403. As used herein, a "plant part" refers to any part of a plant that is comprised of material directly from or derived from a plant comprising event MON87403. Plant parts include but are not limited to cells, pollen, ovules, kernels, flowers, root or stem tissues, fibers, and leaves. Plant parts may be viable, nonviable, regenerable, and/or non-regenerable.

The present disclosure provides a commodity product that is derived from a plant comprising event MON87403. As used herein, a "commodity product" refers to any composition or product that is comprised of material derived from a plant, seed, plant cell, or plant part comprising event MON87403. Commodity products may be sold to consumers and may be viable or nonviable. Nonviable commodity products include but are not limited to nonviable seeds and grains; processed seeds, seed parts, and plant parts; dehydrated plant tissue, frozen plant tissue, and processed plant tissue; seeds and plant parts processed for animal feed for terrestrial and/or aquatic animals consumption, oil, meal, flour, flakes, bran, fiber, milk, cheese, paper, cream, wine, and any other food for human consumption; and biomasses and fuel products. Viable commodity products include but are not limited to seeds and plant cells. A plant comprising event MON87403 can thus be used to manufacture any commodity product typically acquired from a corn plant. Any such commodity product that is derived from the plants comprising event MON87403 may contain at least a detectable amount of the specific and unique DNA corresponding to event MON87403, and specifically may contain a detectable amount of a polynucleotide having a nucleotide sequence of at least 19 consecutive nucleotides of SEQ ID NO:1, at least 18 consecutive nucleotides of SEQ ID NO:2, at least 31 consecutive nucleotides of SEQ ID NO:3, at least 31 consecutive nucleotides of SEQ ID NO:4, at least 51 consecutive nucleotides of SEQ ID NO:5, or at least 51 consecutive nucleotides of SEQ ID NO:6. Any standard method of detection for polynucleotide molecules may be used, including methods of detection disclosed herein. A commodity product is within the scope of the present disclosure if there is any detectable amount of at least 19 consecutive nucleotides of SEQ ID NO:1, at least 18 consecutive nucleotides of SEQ ID NO:2, at least 31 consecutive nucleotides of SEQ ID NO:3, at least 31 consecutive nucleotides of SEQ ID NO:4, at least 51 consecutive nucleotides of SEQ ID NO:5, or at least 51 consecutive nucleotides of SEQ ID NO:6 in the commodity product.

The plant, progeny, seed, plant cell, plant part (such as pollen, ovule, kernel flower, root or stem tissue, and leaf), and commodity products of the present disclosure are therefore useful for, among other things, growing plants for the purpose of producing seed and/or plant parts comprising event MON87403 for agricultural purposes, producing progeny comprising event MON87403 for plant breeding and research purposes, use with microbiological techniques for industrial and research applications, and sale to consumers.

The present disclosure provides methods for producing plants with increased grain yield and plants comprising event MON87403. Event MON87403-containing plants were produced by an *Agrobacterium*-mediated transformation method, using an inbred corn line with the construct pMON97046 (Table 1 and FIG. 3). Construct pMON97046 contains a plant expression cassette for expression of the ATHB17 protein in corn plant cells. Transgenic corn cells were regenerated into intact corn plants and individual plants were selected from the population of independently transformed transgenic plants that showed desirable molecular characteristics, such as single copy of the transgene cassette at a single locus, integrity of the transgene cassette, absence of the construct backbone sequence, and loss of the unlinked glyphosate resistance selection cassette. Furthermore, inverse PCR and DNA sequence analyses were performed to determine the 5' and 3' insert-to-plant genome junctions, to confirm the organization of the elements within the insert (FIG. 1), and to determine the complete DNA sequence of the insert in corn event MON87403 (SEQ ID NO:9). In addition, transgenic plants were screened and selected for increased yield under field conditions. A corn plant that contains in its genome the MON87403 event DNA is an aspect of the present disclosure.

Increased yield of a transgenic plant of the present disclosure can be measured in a number of ways, including test weight, seed number per plant, seed size, seed weight, seed number per unit area (i.e. seeds, or weight of seeds, per acre), bushels per acre, tons per acre, or kilo per hectare. Expression of the ATHB17 gene in plants comprising event MON87403 leads to an increase in grain yield. Expression of the ATHB17 gene in plants comprising event MON87403 also leads to increased ear size at R1.

Methods for producing a plant with increased yield comprising transgenic event MON87403 are provided. Transgenic plants used in these methods may be homozygous or heterozygous for the transgene. Progeny plants produced by these methods may be varietal or hybrid plants; may be grown from seeds produced by a plant and/or from seed comprising event MON87403 produced by a plant fertilized with pollen or ovules from a plant comprising event MON87403; and may be homozygous or heterozygous for the event MON87403 DNA. Progeny plants may be subsequently self-pollinated to generate a true breeding line of plants, i.e., plants homozygous for the event MON87403 DNA, or alternatively may be outcrossed, i.e., bred with another unrelated plant, to produce a varietal or a hybrid seed or plant. As used herein, the term "zygosity" refers to the similarity of DNA at a specific chromosomal location (locus) in a plant. In the present disclosure, the DNA specifically refers to the transgene insert along with the junction sequence (event DNA). A plant is homozygous if the transgene insert with the junction sequence is present at the same location on each chromosome of a chromosome pair (2 alleles). A plant is considered heterozygous if the transgene insert with the junction sequence is present on only one chromosome of a chromosome pair (1 allele). A wild-type plant is null for the event DNA.

A plant with increased yield may be produced by sexually crossing a plant comprising event MON87403 comprising a polynucleotide having the nucleotide sequence of at least 19 consecutive nucleotides of SEQ ID NO:1, at least 18 consecutive nucleotides of SEQ ID NO:2, at least 31 consecutive nucleotides of SEQ ID NO:3, at least 31 consecutive nucleotides of SEQ ID NO:4, at least 51 consecutive nucleotides of SEQ ID NO:5, or at least 51 consecutive nucleotides of SEQ ID NO:6 with another plant and thereby producing seed, which is then grown into progeny plants. These progeny plants may be analyzed using diagnostic methods to select for progeny plants that comprise event MON87403 DNA or for progeny plants with increased yield. The other plant used may or may not be transgenic. The progeny plant and/or seed produced may be varietal or hybrid seed.

A plant with increased yield may be produced by selfing a plant comprising event MON87403 comprising a polynucleotide having the nucleotide sequence of at least 19 consecutive nucleotides of SEQ ID NO:1, at least 18 consecutive nucleotides of SEQ ID NO:2, at least 31 consecutive nucleotides of SEQ ID NO:3, at least 31 consecutive nucleotides of SEQ ID NO:4, at least 51 consecutive nucleotides of SEQ ID NO:5, or at least 51 consecutive nucleotides of SEQ ID NO:6 and thereby producing seed, which is then grown into progeny plants. These progeny plants may then be analyzed using diagnostic methods to select for progeny plants that comprise event MON87403 DNA.

Progeny plants and seeds encompassed by these methods and produced by using these methods are distinct from other plants, for example, because the progeny plants and seeds comprise a recombinant DNA and as such are created by human intervention; contain at least one allele at a specific chromosomal location that comprises the transgenic DNA of the present disclosure; and/or contain a detectable amount of a polynucleotide sequence selected from the group consisting of at least 19 consecutive nucleotides of SEQ ID NO:1, at least 18 consecutive nucleotides of SEQ ID NO:2, at least 31 consecutive nucleotides of SEQ ID NO:3, at least 31 consecutive nucleotides of SEQ ID NO:4, at least 51 consecutive nucleotides of SEQ ID NO:5, or at least 51 consecutive nucleotides of SEQ ID NO:6. A seed may be selected from an individual progeny plant, and so long as the seed comprises SEQ ID NO:1, SEQ ID NO:2, at least 31 consecutive nucleotides of SEQ ID NO:3, at least 31 consecutive nucleotides of SEQ ID NO:4, at least 51 consecutive nucleotides of SEQ ID NO:5, or at least 51 consecutive nucleotides of SEQ ID NO:6, it will be within the scope of the present disclosure.

The plants, progeny, seeds, plant cells, plant parts (such as pollen, ovule, kernel flower, root or stem tissue, and leaves), and commodity products of the present disclosure may be evaluated for DNA composition, gene expression, and/or protein expression. Such evaluation may be done by using various methods such as PCR, sequencing, Northern analysis, Southern analysis, Western analysis, immuno-precipitation, and ELISA or by using the methods of detection and/or the detection kits provided herein.

Methods of detecting the presence of compositions specific to event MON87403 in a sample are provided. One method consists of detecting the presence of DNA specific to and derived from a cell, a tissue, a seed, a plant or plant parts comprising event MON87403. The method provides for a template DNA sample to be contacted with a primer pair that is capable of producing an amplicon from event MON87403 DNA upon being subjected to conditions appropriate for amplification, particularly an amplicon that comprises SEQ ID NO:1, SEQ ID NO:2, at least 31 consecutive nucleotides of SEQ ID NO:3, at least 31 consecutive nucleotides of SEQ ID NO:4, at least 51 consecutive nucleotides of SEQ ID NO:5, or at least 51 consecutive nucleotides of SEQ ID NO:6, or the complements thereof. The amplicon is produced from a template DNA molecule derived from event MON87403, so long as the template DNA molecule incorporates the specific and unique nucleotide sequences of SEQ ID NO:1, SEQ ID NO:2, at least 31 consecutive nucleotides of SEQ ID NO:3, at least 31 consecutive nucleotides of SEQ ID NO:4, at least 51 consecutive nucleotides of SEQ ID NO:5, or at least 51 consecutive nucleotides of SEQ ID NO:6. The amplicon may be single- or double-stranded DNA or RNA, depending on the polymerase selected for use in the production of the amplicon. The method provides for detecting the amplicon molecule produced in any such amplification reaction, and confirming within the sequence of the amplicon the presence of the nucleotides corresponding to SEQ ID NO:1, SEQ ID NO:2, at least 31 consecutive nucleotides of SEQ ID NO:3, at least 31 consecutive nucleotides of SEQ ID NO:4, at least 51 consecutive nucleotides of SEQ ID NO:5, or at least 51 consecutive nucleotides of SEQ ID NO:6, or the complements thereof. The detection of the nucleotides corresponding to SEQ ID NO:1, SEQ ID NO:2, at least 31 consecutive nucleotides of SEQ ID NO:3, at least 31 consecutive nucleotides of SEQ ID NO:4, at least 51 consecutive nucleotides of SEQ ID NO:5, or at least 51 consecutive nucleotides of SEQ ID NO:6, or the complements thereof in the amplicon are determinative and/or diagnostic for the presence of event MON87403 specific DNA and thus biological material or commodity products comprising event MON87403 in the sample.

Another method is provided for detecting the presence of a DNA molecule corresponding to SEQ ID NO:7 or SEQ ID NO:8 in a sample consisting of material derived from plant or plant parts. The method consists of (i) obtaining a DNA sample from a plant or plant part, or from a group of different plants, (ii) contacting the DNA sample with a DNA probe molecule comprising the nucleotides as set forth in either SEQ ID NO:1 or SEQ ID NO:2, (iii) allowing the probe and the DNA sample to hybridize under stringent hybridization conditions, and then (iv) detecting a hybridization event between the probe and the target DNA sample. Detection of the hybrid composition is diagnostic for the presence of SEQ ID NO:7 or SEQ ID NO:8, as the case may be, in the DNA sample. Absence of hybridization is alternatively diagnostic of the absence of the transgenic event in the sample if the appropriate positive controls are run concurrently. Alternatively, determining that a particular plant or plant part comprises either or both of the sequences corresponding to SEQ ID NO:1 or SEQ ID NO:2, or the complements thereof, is determinative that the plant or plant part comprises at least one allele corresponding to event MON87403.

It is thus possible to detect the presence of a nucleic acid molecule of the present disclosure by any well known nucleic acid amplification and detection methods such as polymerase chain reaction (PCR) or another DNA amplification method, or DNA hybridization using nucleic acid probes. An event-specific PCR assay is discussed, for example, by Taverniers et al. (*J. Agric. Food Chem.*, 53: 3041-3052, 2005) in which an event-specific tracing system for transgenic maize lines Bt11, Bt176, and GA21 and for transgenic event RT73 is demonstrated. In this study, event-specific primers and probes were designed based upon the sequences of the genome/transgene junctions for each event. Transgenic plant event specific DNA detection methods have also been described in U.S. Pat. Nos. 6,893,826; 6,825,400; 6,740,488; 6,733,974; 6,689,880; 6,900,014; and 6,818,807.

DNA detection kits are provided. One type of kit contains at least one DNA molecule of sufficient length of contiguous nucleotides of SEQ ID NO:7, SEQ ID NO:9, or SEQ ID NO:10 to function as a DNA primer or probe specific for detecting the presence of DNA derived from transgenic event MON87403 in a sample. The DNA molecule being detected with the kit comprises contiguous nucleotides of the sequence as set forth in SEQ ID NO:1, at least 31 consecutive nucleotides of SEQ ID NO:3, or at least 51 consecutive nucleotides of SEQ ID NO:5. Alternatively, the kit may contain at least one DNA molecule of sufficient length of contiguous nucleotides of SEQ ID NO:8, SEQ ID NO:9, or SEQ ID NO:10 to function as a DNA primer or probe specific for detecting the presence of DNA derived from transgenic event MON87403 in a sample. The DNA molecule being detected with the kit comprises contiguous nucleotides as set forth in SEQ ID NO:2, at least 31 consecutive nucleotides of SEQ ID NO:4, or at least 51 consecutive nucleotides of SEQ ID NO:6. The kit of the invention may optionally include instructions, means for increasing convenience of using the kit such as buffers and test tubes, and the like.

An alternative kit employs a method in which the target DNA sample is contacted with a primer pair as described above, then performing a nucleic acid amplification reaction sufficient to produce an amplicon comprising at least 19 consecutive nucleotides of SEQ ID NO:1, at least 18 consecutive nucleotides of SEQ ID NO:2, at least 31 consecutive nucleotides of SEQ ID NO:3, at least 31 consecutive nucleotides of SEQ ID NO:4, at least 51 consecutive nucleotides of SEQ ID NO:5, or at least 51 consecutive nucleotides of SEQ ID NO:6. Detection of the amplicon and determining the presence of the consecutive nucleotides of SEQ ID NO:1, the consecutive nucleotides of SEQ ID NO:2, at least 31 consecutive nucleotides of SEQ ID NO:3, at least 31 consecutive nucleotides of SEQ ID NO:4, at least 51 consecutive nucleotides of SEQ ID NO:5, or at least 51 consecutive nucleotides of SEQ ID NO:6, or the complements thereof within the sequence of the amplicon is diagnostic for the presence of event MON87403 specific DNA in a DNA sample.

A DNA molecule sufficient for use as a DNA probe is provided that is useful for determining, detecting, or for diagnosing the presence or even the absence of DNA specific and unique to event MON87403 DNA in a sample. The DNA molecule contains the consecutive nucleotides of SEQ ID NO:1, or the complement thereof, the consecutive nucleotides of SEQ ID NO:2, or the complement thereof, at least 31 consecutive nucleotides of SEQ ID NO:3, or the complement thereof, at least 31 consecutive nucleotides of SEQ ID NO:4, or the complement thereof, at least 51 consecutive nucleotides of SEQ ID NO:5, or the complement thereof, or at least 51 consecutive nucleotides of SEQ ID NO:6, or the complement thereof.

Nucleic acid amplification can be accomplished by any of the various nucleic acid amplification methods known in the art, including thermal and isothermal amplification methods. The sequence of the heterologous DNA insert, junction sequences, or flanking sequences from event MON87403 can be verified by amplifying such sequences from the event using primers derived from the sequences provided herein followed by standard DNA sequencing of the amplicon or of the cloned DNA.

The amplicon produced by these methods may be detected by a plurality of techniques. One such method is Genetic Bit Analysis (Nikiforov, et al. *Nucleic Acid Res.* 22:4167-4175, 1994) where a DNA oligonucleotide is designed which overlaps both the adjacent flanking genomic DNA sequence and the inserted DNA sequence. The oligonucleotide is immobilized in wells of a microwell plate. Following thermal amplification of the region of interest (using one primer to the inserted sequence and one to the adjacent flanking genomic sequence), a single-stranded amplicon can be hybridized to the immobilized oligonucleotide and serve as a template for a single base extension reaction using a DNA polymerase and labelled ddNTPs specific for the expected next base. Readout may be fluorescent or ELISA-based. Detection of a fluorescent or other signal indicates the presence of the insert/flanking sequence due to successful amplification, hybridization, and single base extension.

Another method is the pyrosequencing technique as described by Winge (*Innov. Pharma. Tech.* 00:18-24, 2000).

In this method an oligonucleotide is designed that overlaps the adjacent genomic DNA and insert DNA junction. The oligonucleotide is hybridized to a single-stranded amplicon from the region of interest (one primer to the inserted sequence and one to the flanking genomic sequence) and incubated in the presence of a DNA polymerase, ATP, sulfurylase, luciferase, apyrase, adenosine 5' phosphosulfate and luciferin. ddNTPs are added individually and the incorporation results in a light signal which is measured. A light signal indicates the presence of the transgene insert/flanking sequence due to successful amplification, hybridization, and single or multi-base extension.

Fluorescence polarization as described by Chen, et al. (*Genome Res.* 9:492-498, 1999) is a method that can be used to detect the amplicon. Using this method an oligonucleotide is designed which overlaps the genomic flanking DNA and the inserted DNA junction. The oligonucleotide is hybridized to single-stranded amplicon from the region of interest (one primer to the inserted DNA and one to the flanking genomic DNA sequence) and incubated in the presence of a DNA polymerase and a fluorescent-labeled ddNTP. Single base extension results in incorporation of the ddNTP. Incorporation can be measured as a change in polarization using a fluorometer. A change in polarization indicates the presence of the transgene insert/flanking sequence due to successful amplification, hybridization, and single base extension.

TAQMAN® (PE Applied Biosystems, Foster City, Calif.) may also be used to detect and/or to quantify the presence of a DNA sequence using the instructions provided by the manufacturer. Briefly, a FRET oligonucleotide probe is designed which overlaps the genomic flanking DNA and the insert DNA junction. The FRET probe and amplification primers (one primer to the insert DNA sequence and one to the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene insert sequence due to successful amplification and hybridization.

Molecular beacons have been described for use in sequence detection as described in Tyangi et al. (*Nature Biotech.* 14:303-308, 1996). Briefly, a FRET oligonucleotide probe is designed that overlaps the flanking genomic and insert DNA junction. The unique structure of the FRET probe results in it containing secondary structure that keeps the fluorescent and quenching moieties in close proximity. The FRET probe and amplification primers (one primer to the insert DNA sequence and one to the flanking genomic sequence) are cycled in the presence of a thermostable polymerase and dNTPs. Following successful amplification, hybridization of the FRET probe to the target sequence results in the removal of the probe secondary structure and spatial separation of the fluorescent and quenching moieties, which leads to the production of a fluorescent signal. The fluorescent signal indicates the presence of the flanking/transgene insert sequence due to successful amplification and hybridization.

Other described methods, such as microfluidics (U.S. Patent Publication No. 2006/068398; U.S. Pat. No. 6,544,734) provide methods and devices to separate and amplify DNA samples. Optical dyes are used to detect and measure specific DNA molecules (WO/05017181). Nanotube devices (WO/06024023) that comprise an electronic sensor for the detection of DNA molecules or nanobeads that bind specific DNA molecules can then be detected.

DNA detection kits can be developed using the compositions disclosed herein and the methods well-known in the art of DNA detection. The kits are useful for the identification of event MON87403 in a sample and can be applied to methods for breeding plants containing the appropriate event DNA. The kits may contain DNA primers or probes that are similar or complementary to SEQ ID NO:1-6, or fragments or complements thereof.

The kits and detection methods of the present disclosure are therefore useful for, among other things, identifying event MON87403, selecting plant varieties or hybrids comprising event MON87403, detecting the presence of DNA derived from event MON87403 in a sample, and monitoring samples for the presence and/or absence of event MON87403 or plants, plant parts or commodity products comprising event MON87403.

The following examples are included to demonstrate examples of certain embodiments of the disclosure. It should be appreciated by those of skill in the art that the techniques disclosed in the examples that follow represent approaches the inventors have found function well in the practice of the disclosure, and thus can be considered to constitute examples of preferred modes for its practice. However, those of skill in the art should, in light of the present disclosure, appreciate that many changes can be made in the specific embodiments that are disclosed and still obtain a like or similar result without departing from the spirit and scope of the disclosure.

EXAMPLES

Example 1

Transformation of Corn with pMON97046 and Event Selection

This example describes transformation and generation of transgenic corn events, and selection of event MON87403.

Figure 3:
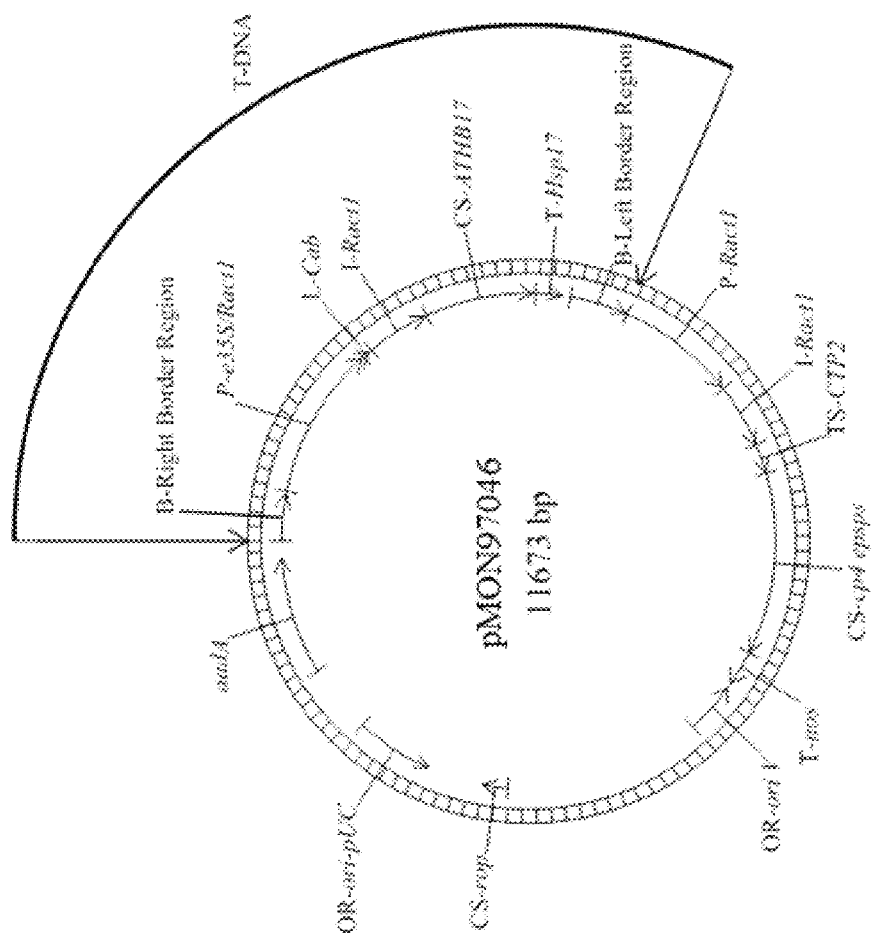
FIG. 3—Shows the plasmid map of transformation vector pMON97046.

An *Agrobacterium*-mediated transformation method was used to transform corn cells with a plasmid vector designated as pMON97046. The construct comprised a right border, an ATHB17 expression cassette, a left border, and a CP4 expression cassette as shown in FIG. 3, as well as other genetic elements necessary for replication and selection in bacteria. The ATHB17 cassette in the transgenic insert as set forth in SEQ ID NO:9 contained the HB17 coding region from *Arabidopsis thaliana* regulated by a CaMV 35S enhancer, a rice actin 1 promoter, a wheat chlorophyll a/b binding protein leader, a rice actin 1 intron, and a hsp17 3' polyadenylation sequence. ATHB17 belongs to the homeodomain leucine zipper (HD-Zip) class II gene family. The CP4 cassette contained a CP4 coding region regulated by a rice actin promoter, leader and intron, and a NOS 3' polyadenylation sequence. The CP4 cassette was used as a selectable marker. Table 1 is a summary of the genetic elements in pMON97046.

TABLE 1

Summary of the genetic elements in pMON97046

| Genetic Element | Location in Plasmid Vector | Function (Reference) |
|---|---|---|
| | | T-DNA |
| B[1]-Right Border Region | 1-357 | DNA region from *Agrobacterium tumefaciens* containing the right border sequence used for transfer of the T-DNA (Depicker et al., 1982; Zambryski et al., 1982) |
| Intervening Sequence | 358-375 | Sequence used in DNA cloning |
| P[2]-e35S/Ract1 | 376-1556 | Chimeric promoter consisting of the duplicated enhancer region from the cauliflower mosaic virus 35S RNA promoter (CaMV) (Kay et al., 1987) combined with the promoter of the act1 gene from *Oryza sativa* that encodes Actin 1 (McElroy et al., 1990) that directs transcription in plant cells |
| Intervening Sequence | 1557-1561 | Sequence used in DNA cloning |
| L[3]-Cab | 1562-1622 | 5' UTR leader sequence from chlorophyll a/b-binding (CAB) protein of *Triticum aestivum* (wheat) that is involved in regulating gene expression |
| Intervening Sequence | 1623-1638 | Sequence used in DNA cloning |
| I[4]-Ract1 | 1639-2118 | Intron and flanking UTR sequence of the act1 gene from *Oryza sativa* (rice) encoding rice Actin 1 protein (McElroy et al., 1991). This sequence is involved in regulating gene expression (McElroy et al., 1991) |
| Intervening Sequence | 2119-2130 | Sequence used in DNA cloning |
| CS[5]-ATHB17 | 2131-2958 | Coding sequence of the ATHB17 gene from *Arabidopsis thaliana* encoding a member of the class II homeodomain-leucine zipper gene family (HD-Zip II) that is thought to act as a transcription factor (Ariel et al., 2007) |
| Intervening Sequence | 2959-2971 | Sequence used in DNA cloning |
| T[6]-Hsp17 | 2972-3181 | 3' UTR sequence from a heat shock protein, Hsp17, of *Triticum aestivum* (wheat) (McElwain and Spiker, 1989) that directs polyadenylation of the mRNA |
| Intervening Sequence | 3182-3234 | Sequence used in DNA cloning |
| B-Left Border Region | 3235-3676 | DNA region from *Agrobacterium tumefaciens* containing the left border sequence used for transfer of the T-DNA (Barker et al., 1983) |
| | | Backbone |
| Intervening Sequence | 3677-3682 | Sequence used in DNA cloning |
| P-Ract1 | 3683-4603 | Promoter and leader of the act1 gene from *Oryza sativa* (rice) encoding the rice Actin 1 protein (McElroy et al., 1990) that directs transcription in plant cells |
| I-Ract1 | 4604-5081 | Intron and flanking UTR sequence of the act1 gene from *Oryza sativa* (rice) encoding rice Actin 1 protein (McElroy et al., 1991). This sequence is involved in regulateing gene expression |
| Intervening Sequence | 5082-5090 | Sequence used in DNA cloning |
| TS[7]-CTP2 | 5091-5318 | Targeting sequence of the ShkG gene from *Arabidopsis thaliana* encoding the EPSPS transit peptide region that directs transport of the protein to the chloroplast (Herrmann, 1995; Klee et al., 1987) |
| CS-cp4 epsps | 5319-6686 | Coding sequence of the aroA gene from *Agrobacterium* sp. strain CP4 encoding the CP4 EPSPS protein that provides herbicide tolerance (Barry et al., 2001); (Padgette et al., 1996) |
| Intervening Sequence | 6687-6701 | Sequence used in DNA cloning |
| T-nos | 6702-6954 | 3' UTR sequence of the nopaline synthase (nos) gene from *Agrobacterium tumefaciens* pTi encoding NOS (Bevan et al., 1983; Fraley et al., 1983), that directs polyadenylation of the mRNA |
| Intervening Sequence | 6955-7005 | Sequence used in DNA cloning |
| OR[8]-ori V | 7006-7402 | Origin of replication from the broad host range plasmid RK2, used for maintenance of plasmid in *Agrobacterium* (Stalker et al., 1981) |

TABLE 1-continued

Summary of the genetic elements in pMON97046

| Genetic Element | Location in Plasmid Vector | Function (Reference) |
| --- | --- | --- |
| Intervening Sequence | 7403-8910 | Sequence used in DNA cloning |
| CS-rop | 8911-9102 | Coding sequence for repressor of primer protein from the ColE1 plasmid for maintenance of plasmid copy number in E. coli (Giza and Huang, 1989) |
| Intervening Sequence | 9103-9529 | Sequence used in DNA cloning |
| OR-ori-pUC | 9530-10118 | Origin of replication from plasmid pUC for maintenance of plasmid in E. coli (Vieira and Messing, 1987) |
| Intervening Sequence | 10119-10648 | Sequence used in DNA cloning |
| aadA | 10649-11537 | Bacterial promoter, coding sequence, and 3' UTR for an aminoglycoside-modifying enzyme, 3"(9)-O-nucleotidyltransferase from the transposon Tn7 (Fling et al., 1985). This sequence confers spectinomycin and streptomycin resistance |
| Intervening Sequence | 11538-11673 | Sequence used in DNA cloning |

Figure 2:
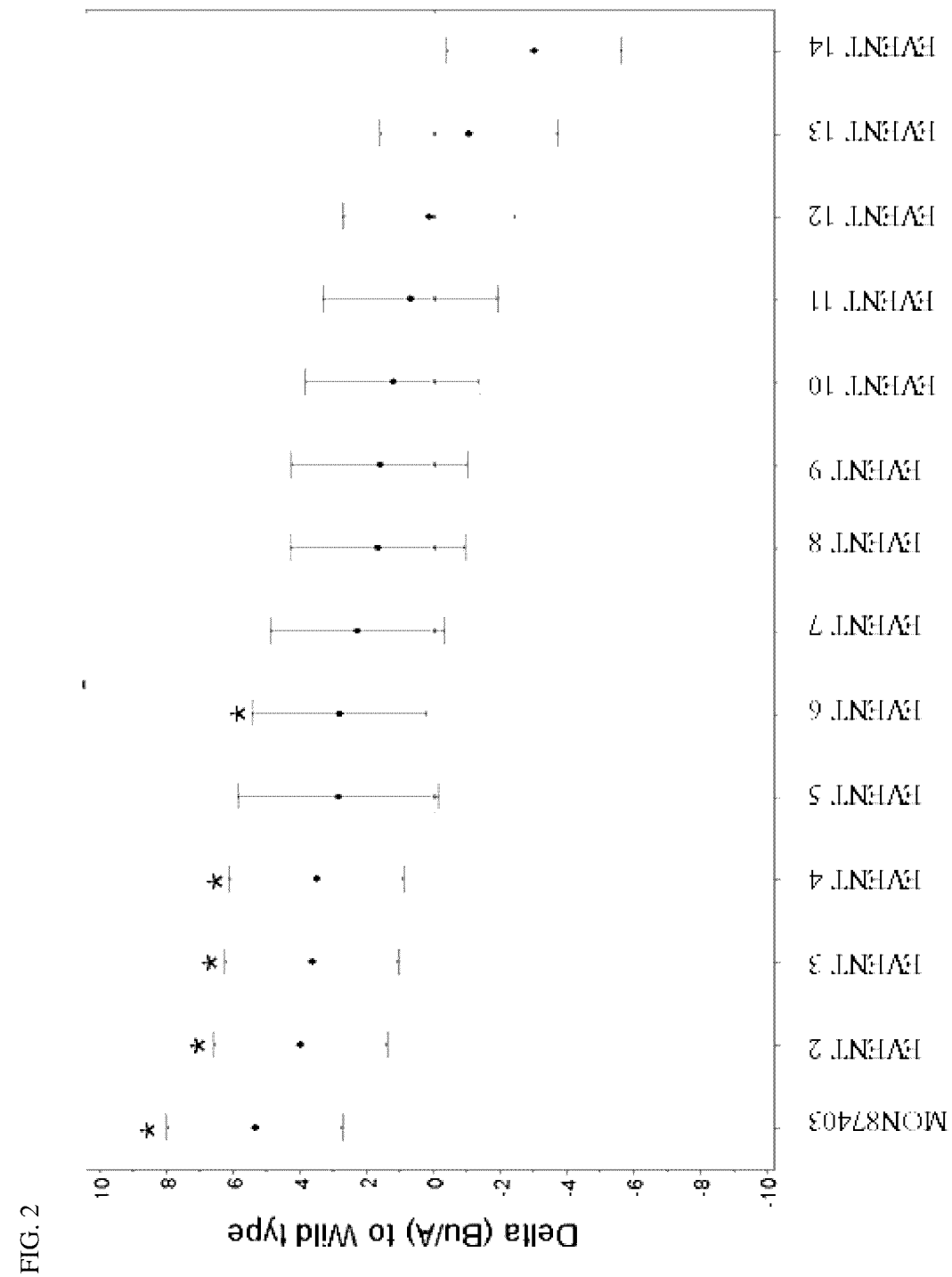
FIG. 2—Shows comparative data of 14 individual events that were advanced to field testing in 2009. Data shown are from the 2009 multi-tester trial taken from 11 locations, with 22 total replicates. Asterisks indicate an event ranked in the top 5.

[1]B, Border
[2]P, Promoter
[3]L, Leader
[4]I, Intron
[5]CS, Coding Sequence
[6]T, Transcription Termination Sequence
[7]TS, Targeting Sequence
[8]OR, Origin of Replication After transformation with construct pMON97046, transformed cells were allowed to grow and multiply on selective media. Plants were regenerated from surviving cells. A total of 2687 independent R0 transformation events were produced and characterized for insert copy number and linkage of ATHB17 with the CP4 cassette. The R1 plant tissue was used for further molecular characterization on insert copy number, linkage to the CP4 expression cassette and the presence of the transformation vector backbone. Events at R3 generation were screened for copy number (the number of copies of the T-DNA within one locus), the integrity of the inserted cassette, the absence of backbone sequence, genomic location of the insert, and expression of the ATHB17 transgene transcript. Events with undesirable phenotypes or molecular characteristics, such as presence of multiple copies of the transgene and/or molecular complexity of the insert, the presence of the transformation vector backbone sequence, and insertion of the transgene in an intragenic region, were eliminated. Furthermore, linkage Southern analysis was done to remove events where the ATHB17 expression cassette was linked to the CP4 selectable marker cassette. No additional elements from the original transformation vector, linked or unlinked to the intact cassettes, were identified in the genome of these events. A total of 324 events met the basic molecular selection criteria based on the R0 analyses and were advanced to R1 generation. Subsequently, 74 events were advanced to the R2 generation, 67 events were advanced to year-1 field trials, 22 events were advanced to the R3 generation, and 15 events were advanced to year-2 field testing. FIG. 2 show comparative data for 14 individual events advanced to field testing in 2009. It was additionally shown that a 155-nt deletion of the genomic DNA occurred upon integration of the MON87403 T-DNA.

Example 2

Isolation of Flanking Sequences Using Inverse PCR and Identification of Flanking Sequences by Sequencing This example describes isolation of the corn genomic DNA sequences flanking the transgenic DNA insert using inverse PCR for event MON87403, and identification of the flanking genomic sequences by sequencing.

Sequences flanking the T-DNA insertion in event MON87403 were determined using inverse PCR. The PCR procedure was followed using genomic DNA from plants comprising event MON87403, using methods known in the art. Primers were located within the Agrobacterium-left border sequence and were SQ6164 (SEQ ID NO:19) and SQ13205 (SEQ ID NO:20), used in that order along with SQ22459 (SEQ ID NO:23) and SQ22458 (SEQ ID NO:22). Amplicons were detected on a 1% TAE agarose gel and samples were sequenced using left border primer SQ6165 (SEQ ID NO:21). The same procedure was followed for the isolation of the right border flank, using primers SQ21173 (SEQ ID NO:24) and SQ22464 (SEQ ID NO:25) for primary, primers SQ22460 (SEQ ID NO:26) and SQ22465 (SEQ ID NO:27) for secondary, and primers SQ22461 (SEQ ID NO:28) and SQ22471 (SEQ ID NO:29) for the tertiary round of PCR.

Amplicons obtained by inverse PCR procedure for the Left and the Right Border reaction for corn event MON87403 were sequenced. The subsequent alignment of the amplicon sequences produced approximately 531 bp of flanking sequence 5' to the Right Border and 277 bp 3' to the left border sequence of the T-DNA.

Short flank sequences (RB and LB flanks) obtained by inverse PCR were subjected to BLAST analysis. The matched genomic sequences were electronically extended along the corn genome beyond 1 kb to obtain virtual extended flanks. The virtually extended flank sequence was then used to design primers for genomic PCR and confirm the actual genomic sequence.

The flanking sequence and wild type sequences were used to design primers for TAQMAN® endpoint assays used to identify the events and determine zygosity as described in Example 3.

Example 3

Event-Specific Endpoint TAQMAN® and Zygosity Assays

This example describes an event-specific endpoint TAQ-MAN® thermal amplification method for identification of event MON87403 DNA in a sample.

Examples of conditions useful with the event MON87403-specific endpoint TAQMAN® method are described in Tables 2 and 3. The DNA primers used in the endpoint assay are primers SQ23846 (SEQ ID NO:11) and SQ4603 (SEQ ID NO:12) and the 6-FAM™ labeled oligonucleotide probe is PB10644 (SEQ ID NO:13). 6FAM™ is a fluorescent dye product of Applied Biosystems (Foster City, Calif.) attached to the DNA probe. For TAQMAN® MGB (Minor Groove Binding) probes, the 5'-exonuclease activity of Taq DNA polymerase cleaves the probe from the 5'-end, between the fluorophore and quencher. When hybridized to the target DNA strand, quencher and fluorophore are separated enough to produce a fluorescent signal.

Primers SQ23846 (SEQ ID NO:11) and SQ4603 (SEQ ID NO:12), when used as described with probe PB10644 (SEQ ID NO:13), produce an amplicon that is diagnostic for event MON87403 DNA. The analysis includes a positive control from corn known to comprise event MON87403 DNA, a negative control from a wild type corn or a corn not comprising event 87403 DNA, and a negative control that contains no template DNA.

These assays are optimized for use with Applied Biosystems GeneAmp PCR System 9700, ABI 9800 Fast Thermal Cycler and MJ Opticon. Other methods and apparatus known to those skilled in the art may be used to produce amplicons that identify the event MON87403 DNA.

TABLE 2

Corn MON87403 Event-Specific Zygosity Endpoint TAQMAN® PCR Conditions

| Step | Reagent | Volume | Comments |
|---|---|---|---|
| 1 | 18 megohm water | adjust for final volume of 10 μl | |
| 2 | 2X Universal Master Mix (dNTPs, enzyme and buffer) | 5.0 μl | 1X final concentration of dNTPs, enzyme and buffer |
| 3 | Event Primers SQ23846 and SQ4603 Mix (resuspended in 18 megohm water to a concentration of 20 μM for each primer) Example: In a microcentrifuge tube, the following are added to achieve: 500 μl at a final concentration of 20 μM 100 μl of Primer SQ23846 at a concentration of 100 μM 100 μl of Primer SQ4603 at a | 0.5 μl | 1.0 μM final concentration |

TABLE 2-continued

Corn MON87403 Event-Specific Zygosity Endpoint TAQMAN® PCR Conditions

| Step | Reagent | Volume | Comments |
|---|---|---|---|
| | concentration of 100 μM 300 μl of 18 megohm water | | |
| 4 | Event 6-FAM™ MGB Probe PB10644 (resuspended in 18 megohm water to a concentration of 10 μM) | 0.2 μl | 0.2 μM final concentration |
| 5 | Wild Type Primer SQ25061 and Wild Type Primer SQ25062 Mix (resuspended in 18 megohm water to a concentration of 20 μM for each primer) | 0.5 μl | 1 μM final concentration |
| 6 | Wild Type VIC™ Probe PB10866 (resuspended in 18 megohm water to a concentration of 10 μM) | 0.2 μl | 0.2 μM final concentration |
| 7 | Extracted DNA (template): 1. Leaf or seed samples to be analyzed 2. Negative control (non-event MON87403 DNA) 3. Negative water control (no template control) 4. Positive control (MON87403 DNA) | 3.0 μl | |

TABLE 3

Endpoint Zygosity TAQMAN® thermocycler conditions

| Cycle No. | Settings |
|---|---|
| 1 | 50° C. 2 minutes |
| 1 | 95° C. 10 minutes |
| 10 | 95° C. 15 seconds |
| | 64° C. 1 minute (−1° C./cycle) |
| 30 | 95° C. 15 seconds |
| | 54° C. 1 minute |
| 1 | 10° C. Forever |

The following example describes an event-specific endpoint TAQMAN® thermal amplification method developed to determine the zygosity of event MON87403 in a sample. A zygosity assay is useful for determining if a plant comprising an event is homozygous, heterozygous or null for the event DNA. An event-comprising plant is homozygous for the event DNA if the transgenic DNA is present at the same location on each chromosome of a chromosomal pair. An event-comprising plant is heterozygous for the event DNA if the transgenic DNA is present on only one chromosome of a chromosomal pair. A plant is null for the event DNA if the plant does not contain the event DNA; that is, the plant is wild type for the locus. A set of primers (SEQ ID NOs:11 and 12, and SEQ ID NOs:14 and 15), a 6FAM™ labeled probe (SEQ ID NO:13), and a VIC™ labeled probe (SEQ ID NO: 16) were used in the assays. These primers are diagnostic. In this example, primers SEQ ID NOs:11 and 12 and the 6FAM™ labeled oligonucleotide probe SEQ ID NO:13 produce a DNA amplicon revealed by the liberation of a fluorescent signal from probe SEQ ID NO:13, which is diagnostic for event MON87403 DNA, indicating at least a copy of the inserted transgenic DNA present in the genomic DNA. Primers SEQ ID NOs:14 and 15 and the VIC™ labeled oligonucleotide probe SEQ ID NO:16 produce an amplicon revealed by the liberation of a fluorescent signal from probe SEQ ID NO:16, which is diagnostic for the wild type allele, indicating no copy of the inserted transgenic DNA present in the genomic DNA. When the primers and probes are mixed together in a PCR with DNA extracted from a plant, release of a fluorescent signal only from the 6FAM™ labeled oligonucleotide probe (SEQ ID NO:13) is indicative of and diagnostic of a plant homozygous for event MON87403. When the primers and probes are mixed together in a PCR with DNA extracted from a plant, release of a fluorescent signal from both the 6FAM™ labeled oligonucleotide probe SEQ ID NO:13 and the VIC™ labeled oligonucleotide probe SEQ ID NO:16 is indicative of and diagnostic of a plant heterozygous for event MON87403. When the primers and probes are mixed together in a PCR with DNA extracted from a plant, release of a fluorescent signal from only the VIC™ labeled oligonucleotide probe SEQ ID NO:16 is indicative of and diagnostic of a plant null for event MON87403, i.e. wild type. The assays also include a positive control from corn containing event MON87403 DNA, a negative control from a wild type corn or corn not comprising event 87403 DNA and a negative control that contains no template DNA.

TABLE 4

Examples of Primer And Probe Combinations Used for Endpoint and Zygosity Assays

| Type | Direction | SEQ ID NO | Sequences |
|---|---|---|---|
| Primers | Reverse | 11 | TGCTCTGTATCCTCCACCATGT |
|  | Forward | 12 | TTTCTCCATATTGACCATCATACTCAT |
| Probe | MON87403 allele | 13 | 6FAM-CTGATCCACATTTCC |
| Primers | Reverse | 14 | GCATGTCTTTAAAAATCCTTGGTTTAC |
|  | Forward | 15 | TGATGTTTTTACTGGATTGCATTACC |
| Probe | Wild type allele | 16 | VIC-CACCCTAAGAGTACTATTGAAGA |

Example 4

Detection of Event MON87403

This example describes how one may identify the MON87403 event within progeny of any breeding event containing MON87403 corn.

Event DNA primer pairs are used to produce an amplicon diagnostic for corn event MON87403. An amplicon diagnostic for MON87403 comprises at least one junction sequence, provided herein as SEQ ID NO:1, SEQ ID NO:2, at least 31 consecutive nucleotides of SEQ ID NO:3, at least 31 consecutive nucleotides of SEQ ID NO:4, at least 51 consecutive nucleotides of SEQ ID NO:5, or at least 51 consecutive nucleotides of SEQ ID NO:6, or the complements thereof ([A] or [B], respectively as illustrated in FIG. 1).

Event primer pairs that produce an amplicon diagnostic for MON87403 include primer pairs designed using the flanking sequences and the integrated transgenic DNA sequence. To acquire a diagnostic amplicon in which at least 19 nucleotides of SEQ ID NO:1 is found, one would design a forward primer based upon the 5' flanking sequence of SEQ ID NO:10 from bases 1 through 1335 and a reverse primer based upon the inserted expression cassette DNA sequence, SEQ ID NO:9, or from positions 1356 through 4477 of SEQ ID NO:10, in which the primers are of sufficient length of contiguous nucleotides to specifically hybridize to SEQ ID NO:10 on either side of the junction sequence. To acquire a diagnostic amplicon in which at least 18 nucleotides of SEQ ID NO:2 is found, one would design a forward primer based upon the inserted expression cassette DNA sequence, SEQ ID NO:9, or from positions 1346 through 4467 of SEQ ID NO:10 and a reverse primer based upon the 3' flanking sequence of SEQ ID NO:10, from bases 4488 through 5744, in which the primers are of sufficient length of contiguous nucleotides to specifically hybridize to SEQ ID NO:10 on either side of the junction sequence. For practical purposes, one should design primers that produce amplicons of a limited size range, for example, between 100 to 1000 bases. Smaller sized (shorter nucleotide length) amplicons in general may be more reliably produced in PCR reactions, allow for shorter cycle times and be easily separated and visualized on agarose gels or adapted for use in endpoint TAQMAN®-like assays. In addition, amplicons produced using primer pairs can be cloned into vectors, propagated, isolated and sequenced or can be sequenced directly with methods well-established in the art. Any primer pair derived from the combination of flanking sequences and the integrated transgenic DNA sequence from SEQ ID NO:10 that are useful in a DNA amplification method to produce an amplicon diagnostic for MON87403, plants comprising MON87403 or progeny thereof is an aspect of the present disclosure. Any single isolated DNA primer molecule comprising a sufficient length of contiguous nucleotides, for instance, at least 11 contiguous nucleotides of SEQ ID NO:10, or its complement that is useful in a DNA amplification method to produce an amplicon diagnostic for MON87403, plants comprising MON87403 or progeny thereof is an aspect of the present disclosure. In another embodiment, the present disclosure provides isolated DNA primer molecules diagnostic for MON87403 comprising a combination of flanking sequences and integrated transgenic DNA sequence from SEQ ID NO:7 or 8.

An example of the amplification conditions for this analysis is illustrated in Tables 2 and 3. However, any modification of these methods or the use of DNA primers homologous or complementary to SEQ ID NO:7, 8, and 10 that produce an amplicon diagnostic for MON87403 is within the scope of the present disclosure. A diagnostic amplicon comprises a DNA molecule homologous or complementary to at least one transgene/genomic junction DNA (SEQ ID NO:1, SEQ ID NO:2, at least 31 consecutive nucleotides of SEQ ID NO:3, at least 31 consecutive nucleotides of SEQ ID NO:4, at least 51 consecutive nucleotides of SEQ ID NO:5, or at least 51 consecutive nucleotides of SEQ ID NO:6, or the complements thereof), or a substantial portion thereof.

An analysis for event MON87403 DNA in a sample should include a positive control from event MON87403, a negative control from a corn plant that does not contain event MON87403, for example, but not limited to wild type control, and a negative control that contains no corn genomic DNA. A primer pair that will amplify an endogenous corn DNA molecule will serve as an internal control for the DNA amplification conditions. Additional primer sequences can be selected from SEQ ID NOs:7, 8, and 10 bp those skilled in the art of DNA amplification methods, and conditions selected for the production of an amplicon by the methods shown in Tables 2 and 3 may differ, but result in an amplicon diagnostic for event MON87403 DNA. The use of these DNA primer sequences with modifications to the methods of Table 2 and 3 are within the scope of the disclosure. The amplicon produced by at least one DNA primer sequence derived from SEQ ID NOs:7, 8, and 10 that is diagnostic for MON87403 is an aspect of the disclosure.

DNA detection kits that contain at least one DNA primer derived from SEQ ID NOs:7, 8, and 10 that when used in a DNA amplification method, produces a diagnostic amplicon for MON87403, plants comprising MON87403 or progeny thereof is an aspect of the disclosure. A corn plant or seed, wherein its genomic DNA produces an amplicon diagnostic for MON87403 when tested in a DNA amplification method is an aspect of the disclosure. The assay for the MON87403 amplicon can be performed by using an Applied Biosytems GeneAmp PCR System 9700, ABI 9800 Fast Thermal Cycler and MJ Opticon, Stratagene Robocycler, MJ Engine, Perkin-Elmer 9700 or Eppendorf Mastercycler Gradient thermocycler or any other amplification system that can be used to produce an amplicon diagnostic of MON87403.

A representative sample of seed comprising event MON87403 disclosed above and recited in the claims has been deposited according to the Budapest Treaty with the ATCC. The date of deposit was Mar. 1, 2013, and the ATCC accession number is PTA-13584. Upon issuance of a patent, all restrictions upon the deposit will be removed, and the deposit is intended to meet all of the requirements of 37 C.F.R. §§1.801-1.809. The deposit will be maintained in the depository for a period of 30 years, or 5 years after the last request, or for the effective life of the patent, whichever is longer, and will be replaced as necessary during that period.

Example 5

Plants Comprising the MON87403 Event Exhibit Increased Yield

Figure 4:
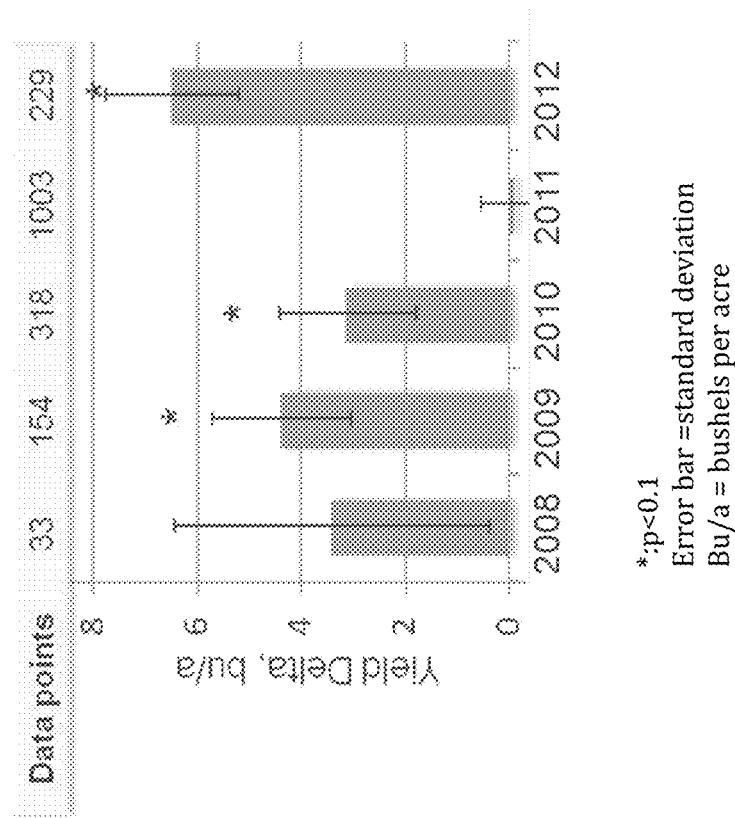
FIG. 4—Shows the increased yield performance of plants comprising the MON87403 event in transformation germplasm-based hybrids across years.

Plants comprising the MON87403 event were planted over multiple locations in multiple testers for several years under optimal production management practices and maximum weed and pest control. The data in FIG. 4 show that plants comprising the MON87403 event exhibited a mean yield advantage across locations in all but one year, as compared to the appropriate control plants.

Example 6

Plants Comprising the MON87403 Event Exhibit Increased R1 Ear Weight

To investigate the effect of expression of the ATHB17 gene on the R1 ear weight, data were collected from field trials conducted within the major U.S. maize production region. Plants comprising the MON87403 event were compared to a near isogenic conventional control across 13 U.S. locations in 2012 for comparison of the ear weight at the R1 stage. The experiment was planted in a randomized complete block design with 4 replications per site. Data was collected from 13 sites (N=51). Plants were sampled by separating the primary ear from the plant. Ears were dried in a forced air oven at 80° C. until constant weight prior to weighing. A statistically significant increase in R1 ear weight was observed in plants comprising the MON87403 event compared to the conventional control in a combined site analysis (Table 5).

TABLE 5

Combined site analysis of R1 ear weight from plants comprising the MON87403 event and the conventional control from U.S. field trials

| Characteristic (units) | MON 87403 (Mean ± SE) | Control (Mean ± SE) | Difference | p-value |
| --- | --- | --- | --- | --- |
| R1 ear weight (g) | 144.5 (±8.5) | 129.3 (±8.1) | 15.2 | 0.004 |

Having illustrated and described the principles of the present disclosure, it should be apparent to persons skilled in the art that the disclosure can be modified in arrangement and detail without departing from such principles. We claim all modifications that are within the spirit and scope of the appended claims.

What is claimed is:

1. A recombinant DNA molecule comprising a nucleotide sequence selected from the group consisting of SEQ ID NO:1, SEQ ID NO:3, SEQ ID NO:5, SEQ ID NO:7, SEQ ID NO:10, and full complements thereof.

2. The recombinant DNA molecule of claim 1, wherein said recombinant DNA molecule is formed by the junction of an inserted heterologous nucleic acid molecule and genomic DNA of a corn plant, plant cell, or seed.

3. The recombinant DNA molecule of claim 1, wherein said DNA molecule is from a transgenic corn plant comprising event MON87403, a representative sample of seed comprising said event having been deposited as ATCC Accession No. PTA-13584.

4. The recombinant DNA molecule of claim 1, wherein said DNA molecule is an amplicon diagnostic for the presence of DNA from transgenic corn event MON87403.

5. The recombinant DNA molecule of claim 1, wherein said recombinant DNA molecule is in a corn plant, plant cell, seed, progeny plant, plant part, or commodity product.

6. A transgenic corn plant, seed, cell, or plant part thereof comprising the recombinant DNA molecule of claim 1.

7. A transgenic corn plant, seed, cell, or plant part thereof, wherein said plant, seed, cell, or plant part thereof has increased yield as compared to a control corn plant, seed, cell, or plant part thereof, and wherein said corn plant, seed, cell, or plant part thereof comprises event MON87403, a representative sample of seed comprising said event having been deposited as ATCC Accession No. PTA-13584.

8. The transgenic corn plant, seed, cell, or plant part thereof of claim 6, the genome of which produces an amplicon comprising a DNA molecule selected from the group consisting of SEQ ID NO:1, SEQ ID NO:3, SEQ ID NO:5, SEQ ID NO:7, and SEQ ID NO:10 when tested in a DNA amplification method.

9. A corn plant or seed, comprising event MON87403, a representative sample of seed comprising said event having been deposited under ATCC Accession No. PTA-13584.

10. The corn plant or seed of claim 9, wherein said corn plant or seed is a hybrid having at least one parent comprising event MON87403.

11. A nonliving plant material comprising the recombinant DNA molecule of claim 1.

12. A microorganism comprising the recombinant DNA molecule of claim 1.

13. The microorganism of claim 12, wherein said microorganism is a plant cell.

14. A method of increasing yield in a corn plant comprising:

(a) planting a transgenic corn plant or transgenic corn seed comprising event MON87403, a representative sample of seed comprising said event having been deposited as ATCC Accession No. PTA-13584; and (b) growing said transgenic corn plant or transgenic corn seed to obtain increase in yield in said corn plant as compared to a control corn plant.

15. A method of producing a corn plant with increased yield comprising:

(a) sexually crossing a transgenic corn plant comprising event MON87403, a representative sample of seed comprising said event having been deposited as ATCC Accession No. PTA-13584 with a second corn plant, thereby producing seed;

(b) collecting said seed produced from said cross;

(c) growing said seed to produce a plurality of progeny corn plants; and (d) selecting a progeny corn plant comprising said event MON87403 that has increased yield as compared to a control corn plant.

16. A method of producing a corn plant with increased yield comprising:

(a) selfing a transgenic corn plant comprising event MON87403, a representative sample of seed comprising said event having been deposited as ATCC Accession No. PTA-13584, thereby producing seed;

(b) collecting said seed produced from said selfing;

(c) growing said seed to produce a plurality of progeny corn plants; and (d) selecting a progeny corn plant comprising said event MON87403 that has increased yield as compared to a control corn plant.

17. A method of producing hybrid corn seed comprising:

(a) sexually crossing a transgenic corn plant comprising event MON87403, a representative sample of seed comprising said event having been deposited as ATCC Accession No. PTA-13584 with a second corn plant, thereby producing hybrid corn seed; and (b) selecting hybrid corn seed comprising said event MON87403.

18. The recombinant DNA molecule of claim 1, comprising the nucleotide sequence of SEQ ID NO:1.

19. The recombinant DNA molecule of claim 1, comprising the nucleotide sequence of SEQ ID NO:3.

20. The recombinant DNA molecule of claim 1, comprising the nucleotide sequence of SEQ ID NO:5.

21. The recombinant DNA molecule of claim 1, comprising the nucleotide sequence of SEQ ID NO:7.

22. The recombinant DNA molecule of claim 1, comprising the nucleotide sequence of SEQ ID NO:10.

* * * * *